United States Patent
Wu et al.

(10) Patent No.: US 9,878,161 B2
(45) Date of Patent: Jan. 30, 2018

(54) ENTRAINMENT OF BIOELECTRICAL BRAIN SIGNALS

(75) Inventors: Jianping Wu, Shoreview, MN (US); Steven L. Jensen, Andover, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1236 days.

(21) Appl. No.: 13/446,801

(22) Filed: Apr. 13, 2012

(65) Prior Publication Data

US 2012/0277820 A1 Nov. 1, 2012

Related U.S. Application Data

(60) Provisional application No. 61/480,551, filed on Apr. 29, 2011.

(51) Int. Cl.
*A61N 1/00* (2006.01)
*A61N 1/36* (2006.01)

(52) U.S. Cl.
CPC ..... *A61N 1/36171* (2013.01); *A61N 1/36067* (2013.01); *A61N 1/36139* (2013.01)

(58) Field of Classification Search
CPC .............. A61N 1/36082; A61N 1/3606; A61N 1/36067; A61N 1/36025
USPC .................................................. 607/45, 2, 1
See application file for complete search history.

(56) References Cited

U.S. PATENT DOCUMENTS

| 4,227,516 | A | 10/1980 | Meland et al. |
| 4,753,246 | A | 6/1988 | Freeman |
| 4,776,345 | A | 10/1988 | Cohen et al. |
| 5,299,569 | A | 4/1994 | Wernicke et al. |
| 6,157,857 | A | 12/2000 | Dimpfel |
| 6,167,298 | A | 12/2000 | Levin |
| 6,200,273 | B1 | 3/2001 | Sininger |
| 6,227,203 | B1 | 5/2001 | Rise et al. |

(Continued)

OTHER PUBLICATIONS

Loddenkkemper, et al., "Circadian Patterns of Pediatric Seizures," Neurology 76, Jan. 11, 2011: 145-153.

(Continued)

*Primary Examiner* — Amanda Patton
*Assistant Examiner* — Philip C Edwards
(74) *Attorney, Agent, or Firm* — Shumaker & Sieffert, P.A.

(57) ABSTRACT

The disclosure relates to the delivery of electrical stimulation therapy to the brain of a patient, e.g., to treat or otherwise manage a patient disorder. In one example, the disclosure relates to a method comprising generating electrical stimulation via a medical device; delivering the electrical stimulation at a first frequency to a brain of a patient when the bioelectrical brain signals of the patient oscillate at a second frequency, where the second frequency corresponds to pathological brain signals of the patient, where the electrical stimulation is selected to entrain the bioeiectrical brain signals of the patient; and adjusting the delivered electrical stimulation from the first frequency to a third frequency, where adjusting the delivered electrical stimulation changes the bioelectrical brain signal oscillations to a fourth frequency different from the second frequency. The fourth frequency may correspond to an oscillation frequency of non-pathological brain signals of the patient.

28 Claims, 9 Drawing Sheets

(56) References Cited

U.S. PATENT DOCUMENTS

| | | |
|---|---|---|
| 6,402,520 B1 | 6/2002 | Freer |
| 6,453,193 B1 | 9/2002 | Heyrend et al. |
| 6,615,076 B2 | 9/2003 | Mitra |
| 6,920,351 B2 | 7/2005 | Mitra |
| 7,006,872 B2 | 2/2006 | Gielen et al. |
| 7,089,059 B1 | 8/2006 | Pless |
| 7,120,486 B2 | 10/2006 | Leuthardt |
| 7,171,339 B2 | 1/2007 | Repucci |
| 7,257,439 B2 | 8/2007 | Llinas |
| 7,280,867 B2 | 10/2007 | Osorio et al. |
| 7,341,562 B2 | 3/2008 | Pless |
| 7,392,079 B2 | 6/2008 | Donoghue |
| 7,409,321 B2 | 8/2008 | Repucci |
| 7,532,935 B2 | 5/2009 | Maschino et al. |
| 7,577,472 B2 | 8/2009 | Li et al. |
| 7,626,015 B2 | 12/2009 | Feinstein |
| 7,668,591 B2 | 2/2010 | Lee et al. |
| 7,734,340 B2 | 6/2010 | DeRidder |
| 7,747,318 B2 | 6/2010 | John |
| 7,801,601 B2 | 9/2010 | Maschino et al. |
| 7,818,065 B2 | 10/2010 | Llinas |
| 7,819,812 B2 | 10/2010 | John |
| 7,892,182 B2 | 2/2011 | Pless |
| 7,894,890 B2 | 2/2011 | Sun et al. |
| 7,894,903 B2 | 2/2011 | John |
| 7,937,138 B2 | 5/2011 | Liley |
| 8,017,764 B2 | 9/2011 | Feinstein |
| 8,073,534 B2 | 12/2011 | Low |
| 8,078,281 B2 | 12/2011 | Foffani |
| 8,090,674 B2 | 1/2012 | Ginosar |
| 8,140,152 B2 | 3/2012 | John |
| 2001/0003145 A1 | 6/2001 | Mori et al. |
| 2004/0073129 A1 | 4/2004 | Caldwell et al. |
| 2004/0073273 A1 | 11/2004 | Gluckman et al. |
| 2005/0033154 A1 | 2/2005 | deCharms |
| 2005/0154424 A1 | 7/2005 | Tass |
| 2005/0197560 A1 | 9/2005 | Rao et al. |
| 2005/0209512 A1 | 9/2005 | Heruth et al. |
| 2005/0215884 A1 | 9/2005 | Greicius et al. |
| 2005/0283053 A1 | 12/2005 | deCharms |
| 2006/0155348 A1 | 7/2006 | deCharms |
| 2006/0173259 A1 | 8/2006 | Flaherty |
| 2006/0212090 A1 | 9/2006 | Lozano et al. |
| 2007/0067003 A1 | 3/2007 | Sanchez |
| 2007/0123758 A1 | 5/2007 | Miesel et al. |
| 2007/0142874 A1* | 6/2007 | John ............................... 607/45 |
| 2007/0191704 A1 | 8/2007 | deCharms |
| 2007/0225674 A1 | 9/2007 | Molnar et al. |
| 2007/0244407 A1 | 10/2007 | Osorio |
| 2008/0001600 A1 | 1/2008 | deCharms |
| 2008/0015459 A1 | 1/2008 | Llinas |
| 2008/0045775 A1 | 2/2008 | Lozano |
| 2008/0071150 A1 | 3/2008 | Miesel et al. |
| 2008/0077039 A1 | 3/2008 | Donnett |
| 2008/0243022 A1 | 10/2008 | Donnett |
| 2008/0269631 A1 | 10/2008 | Denison et al. |
| 2009/0082691 A1 | 3/2009 | Denison et al. |
| 2009/0099623 A1 | 4/2009 | Bentwich |
| 2009/0105521 A1 | 4/2009 | Bentwich |
| 2009/0124919 A1 | 5/2009 | Ginosar et al. |
| 2009/0163982 A1 | 6/2009 | deCharms |
| 2009/0177144 A1 | 7/2009 | Masmanidis |
| 2009/0179642 A1 | 7/2009 | deCharms |
| 2009/0192556 A1 | 7/2009 | Wu et al. |
| 2009/0196471 A1 | 8/2009 | Goetz |
| 2009/0220425 A1 | 9/2009 | Moxon |
| 2009/0318794 A1 | 12/2009 | deCharms |
| 2009/0318826 A1 | 12/2009 | Green et al. |
| 2010/0069739 A1 | 3/2010 | deCharms |
| 2010/0100153 A1 | 4/2010 | Carlson |
| 2010/0114237 A1 | 5/2010 | Giftakis et al. |
| 2010/0121213 A1 | 5/2010 | Giftakis |
| 2010/0121214 A1 | 5/2010 | Giftakis |
| 2010/0121215 A1 | 5/2010 | Giftakis |
| 2010/0135553 A1 | 6/2010 | Joglekar |
| 2010/0137937 A1 | 6/2010 | John et al. |
| 2010/0218454 A1 | 9/2010 | Detjen |
| 2010/0241020 A1 | 9/2010 | Zaidel et al. |
| 2010/0262205 A1 | 10/2010 | DeRidder |
| 2010/0280334 A1 | 11/2010 | Carlson et al. |
| 2010/0280335 A1 | 11/2010 | Carlson et al. |
| 2010/0280336 A1 | 11/2010 | Giftakis et al. |
| 2010/0280403 A1 | 11/2010 | Erdogmus |
| 2010/0286748 A1 | 11/2010 | Midani |
| 2011/0105584 A1 | 5/2011 | Feinstein et al. |
| 2011/0130797 A1 | 6/2011 | Talathi et al. |
| 2011/0137371 A1 | 6/2011 | Giftakis et al. |
| 2011/0144716 A1 | 6/2011 | Bikson et al. |
| 2011/0184489 A1 | 7/2011 | Nicolelis et al. |
| 2011/0196446 A1 | 8/2011 | Wu et al. |
| 2011/0257715 A1 | 10/2011 | Jarosh et al. |

OTHER PUBLICATIONS

Eusebio, et al., "Resonance in Subthalamo-Cortical Circuits in Parkinson's Disease", Brain 2009, pp. 1-12.

Garrett et al., The Importance of Being Variable, the Journal of Neuroscience, Mar. 23, 2011, 31(12): 4496-4503.

Keimel et al., "Development Proposal: A Low Cost System for fMRI and Spectroscopic Screening and Monitoring of Alzheimer's Disease", Advanced Function Biomedical Imaging, University of Minnesota, Fall 2008, Dec. 12, 2008.

Lynall et al., "Functional Connectivity and Brain Networks in Schizophrenia", J. Neuroscience, Jul. 14, 2010—30(28):9477-9487.

Pihlajamaki et al., "Functional MRI Assessment of Task-Induced Deactivation of the Default Mode Network in Alzheimer's Disease and At-Risk Older Individuals," Behavioral Neurology 21 (1) (2009) 77-91.

Sperling, et al., "Functional Alterations in Memory Networks in Early Alzheimer's Disease," Neuromol Med (2010) 12:27-43.

Van Veen, et al., "Localization of Brain Electrical Activity via Linearly Constrained Minimum Variance Spatial Filtering" IEEE Transactions on Biomedical Engineering, vol. 44, No. 9, Sep. 1997.

Westlye, et al., "Increased hippocampal Default Mode Synchronization During Rest in Middle-Aged and Elderly APOE, ϵ4 Carriers: Relationships with Memory Performance," the Journal of Neuroscience, May 25, 2011, 31(21): 7775-7783.

* cited by examiner

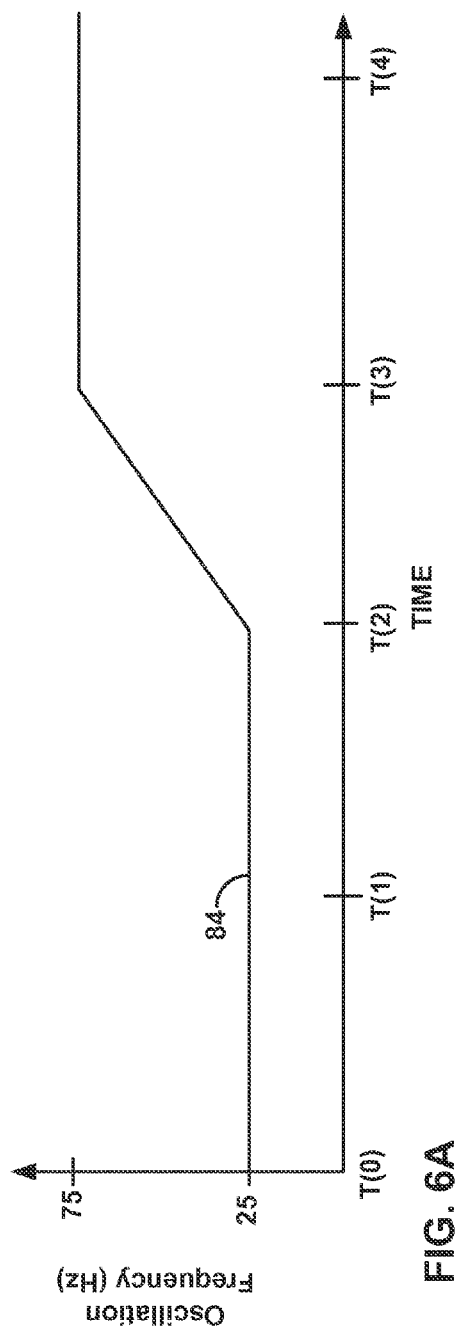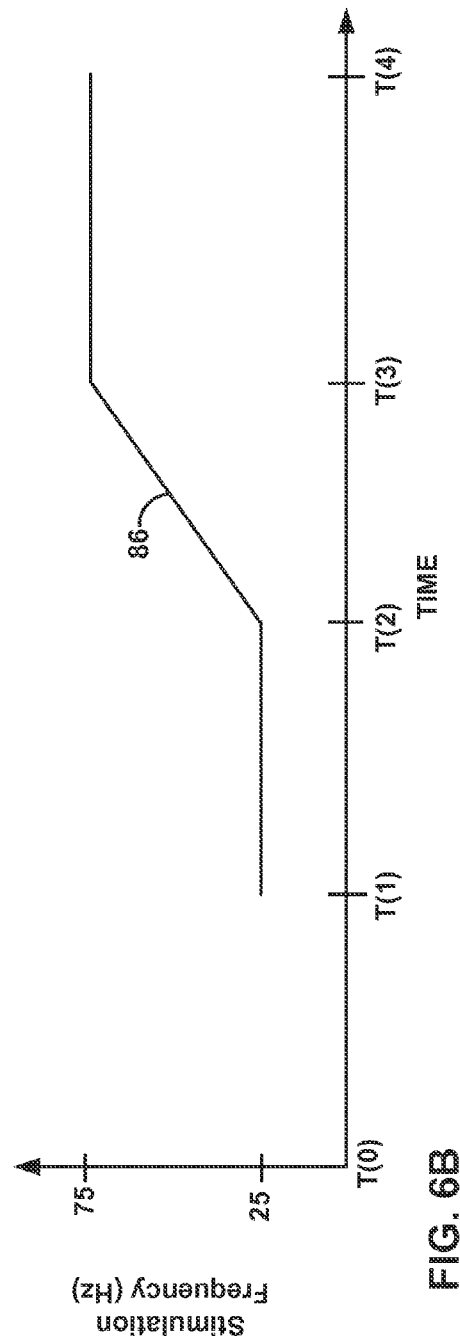

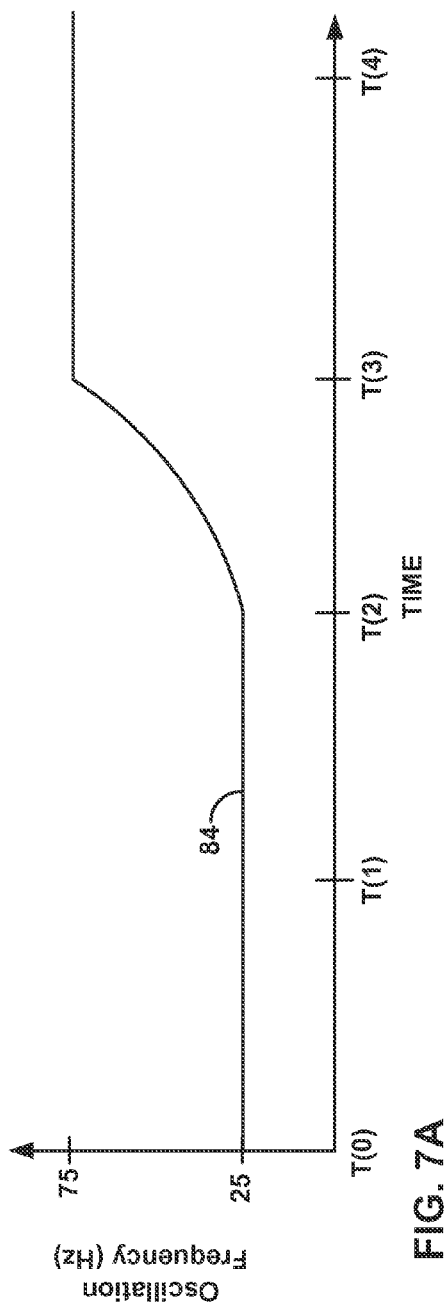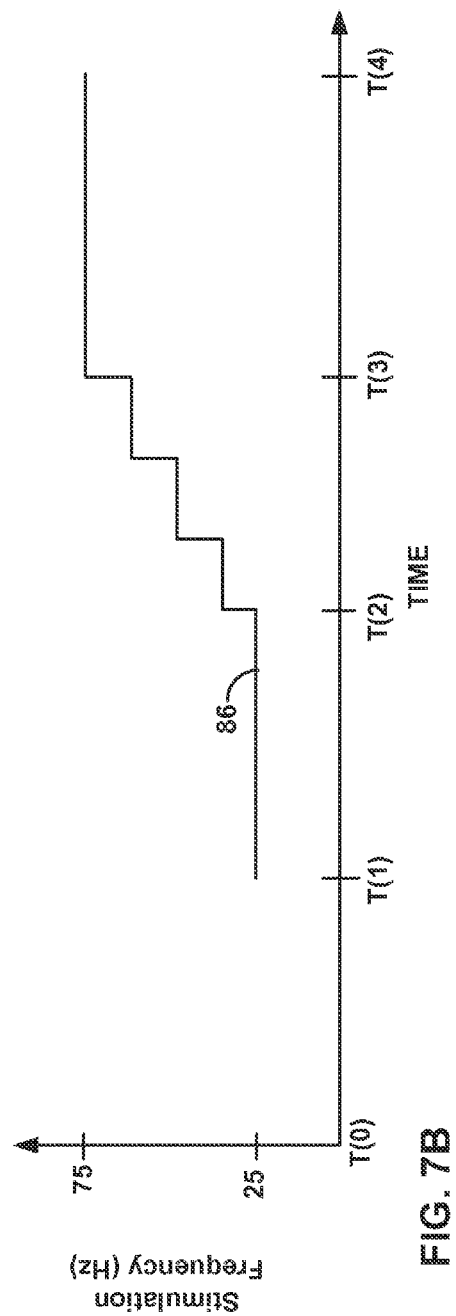

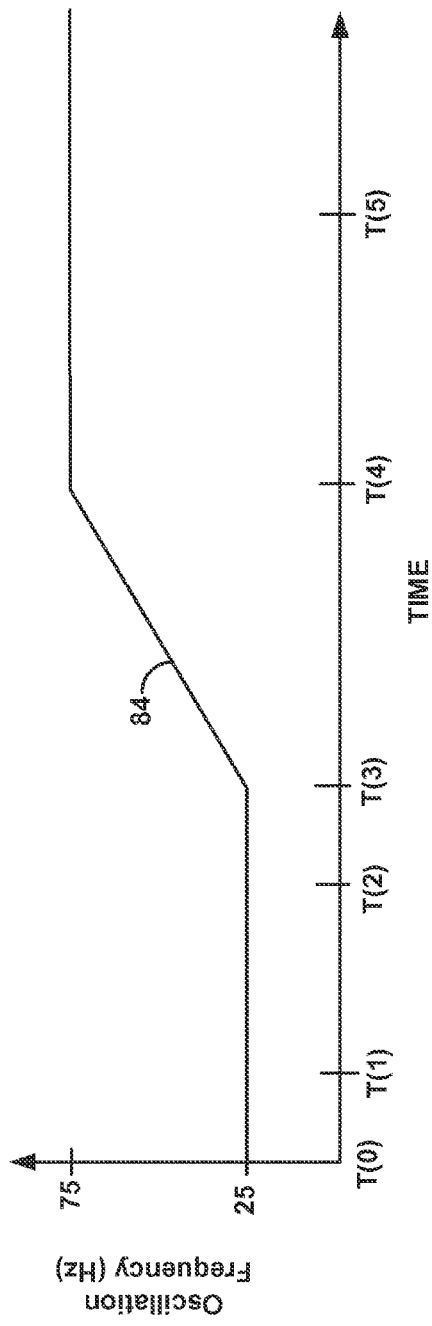
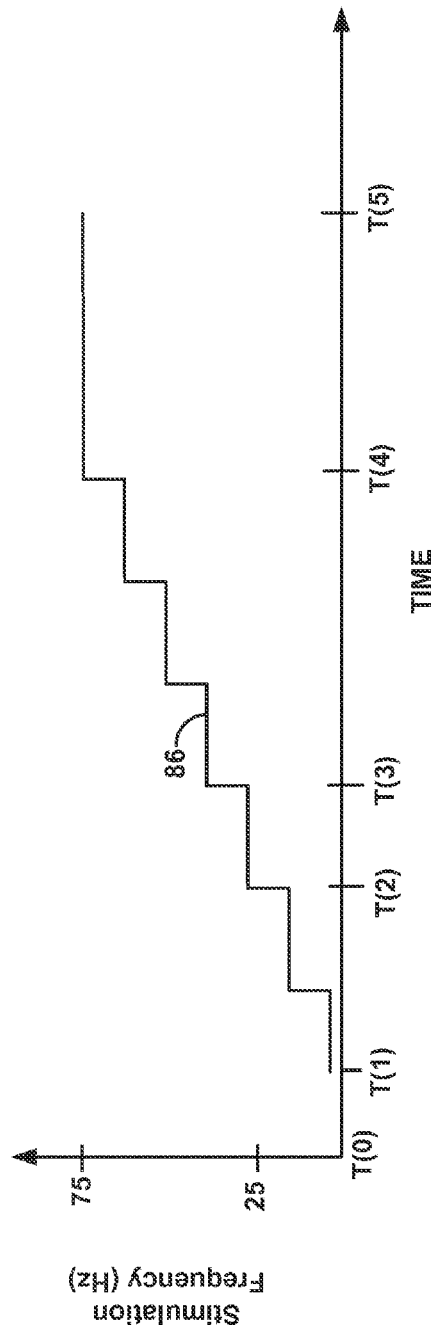
FIG. 8A
FIG. 8B

ENTRAINMENT OF BIOELECTRICAL BRAIN SIGNALS

This application claims the benefit of U.S. Provisional Application No. 61/480,551, entitled "ENTRAINMENT OF BIOELECTRICAL BRAIN SIGNALS," and filed on Apr. 29, 2011, the entire content of which is incorporated herein by reference.

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) by a medical device to one or more sites in a patient, such as a brain, spinal cord, leg muscle or arm muscle, in a patient may help alleviate, and in some cases, eliminate symptoms associated with movement disorders.

SUMMARY

In general, the disclosure relates to systems, devices, and techniques for delivering electrical stimulation via a medical device to the brain of a patient to modify the oscillation frequency of bioelectrical brain signals of the patient. In some examples, the bioelectrical brain signals may oscillate at a frequency that corresponds to pathological brain signals of the patient. When the biological brain signals of the patient oscillate at such a frequency, a medical device may deliver electrical stimulation (e.g., in the form of pulses or continuous waveform) to the brain at a frequency selected to entrain the bioelectrical brain activity. When entrained, the frequency of the delivered electrical stimulation may then be adjusted to a different frequency to change the oscillation frequency of the bioelectrical brain signals of the patient. For example, the frequency of the delivered electrical stimulation may be adjusted to a frequency corresponding to non-pathological brain signals. In this manner, the bioelectrical brain signals of the patient may be modified via the delivered electrical stimulation from an oscillation frequency of pathological brain signals to an oscillation frequency of non-pathological brain signals.

In one example, the disclosure is directed to a method comprising delivering electrical stimulation from a medical device at a first frequency to a brain of a patient when bioelectrical brain signals of the patient oscillate at a second frequency, wherein the second frequency corresponds to pathological brain signals of the patient, and wherein the electrical stimulation is selected to entrain the bioelectrical brain signals of the patient; and adjusting the delivered electrical stimulation from the first frequency to a third frequency, wherein adjusting the delivered electrical stimulation changes the oscillation of the bioelectrical brain signals to a fourth frequency different from the second frequency.

In another example, the disclosure is directed to a medical device system comprising an electrical stimulation generator configured to generate electrical stimulation; and a processor configured to control the electrical stimulation generator to generate and deliver the electrical stimulation at a first frequency to a brain of a patient when bioelectrical brain signals of the patient oscillate at a second frequency, and adjust the delivered electrical stimulation from the first frequency to a third frequency, wherein the second frequency corresponds to pathological brain signals of the patient, wherein the electrical stimulation is selected to entrain the bioelectrical brain signals of the patient, and wherein adjusting the delivered electrical stimulation changes the oscillation of the bioelectrical brain signals to a fourth frequency different from the second frequency.

In another example, the disclosure is directed to a system comprising means for delivering the electrical stimulation at a first frequency to a brain of a patient when bioelectrical brain signals of the patient oscillate at a second frequency, wherein the second frequency corresponds to pathological brain signals of the patient, and wherein the electrical stimulation is selected to entrain the bioelectrical brain signals of the patient; and means for adjusting the delivered electrical stimulation from the first frequency to a third frequency, wherein the means for adjusting the delivered electrical stimulation changes the oscillation of the biociectrical brain signals to a fourth frequency different from the second frequency.

In another example, the disclosure is directed to a non-transitory computer-readable storage medium comprising instructions that cause one or more processors to control delivery of the electrical stimulation at a first frequency to a brain of a patient when bioelectrical brain signals of the patient oscillate at a second frequency, wherein the second frequency corresponds to pathological brain signals of the patient, and wherein the electrical stimulation is selected to entrain the bioelectrical brain signals of the patient; and adjust the delivered electrical stimulation from the first frequency to a third frequency, wherein adjusting the delivered electrical stimulation changes the oscillation of the bioelectrical brain signals to a fourth frequency different from the second frequency.

In another example, the disclosure relates to a non-transitory computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform one or more of the techniques described herein.

The details of one or more aspects of the disclosure are set forth in the accompanying drawings and the description below. Other features, objects, and advantages will be apparent from the description and drawings, and from the claims.

BRIEF DESCRIPTION OF THE DRAWINGS

FIGS. 6A and 6B are graphs illustrating frequency versus time for example bioelectrical brain signals and example electrical stimulation therapy, respectively.

FIGS. 7A and 7B are graphs illustrating frequency versus time for example bioelectrical brain signals and example electrical stimulation therapy, respectively.

FIGS. 8A and 8B are graphs illustrating frequency versus time for example bioelectrical brain signals and example electrical stimulation therapy, respectively.

DETAILED DESCRIPTION

Figure 1:
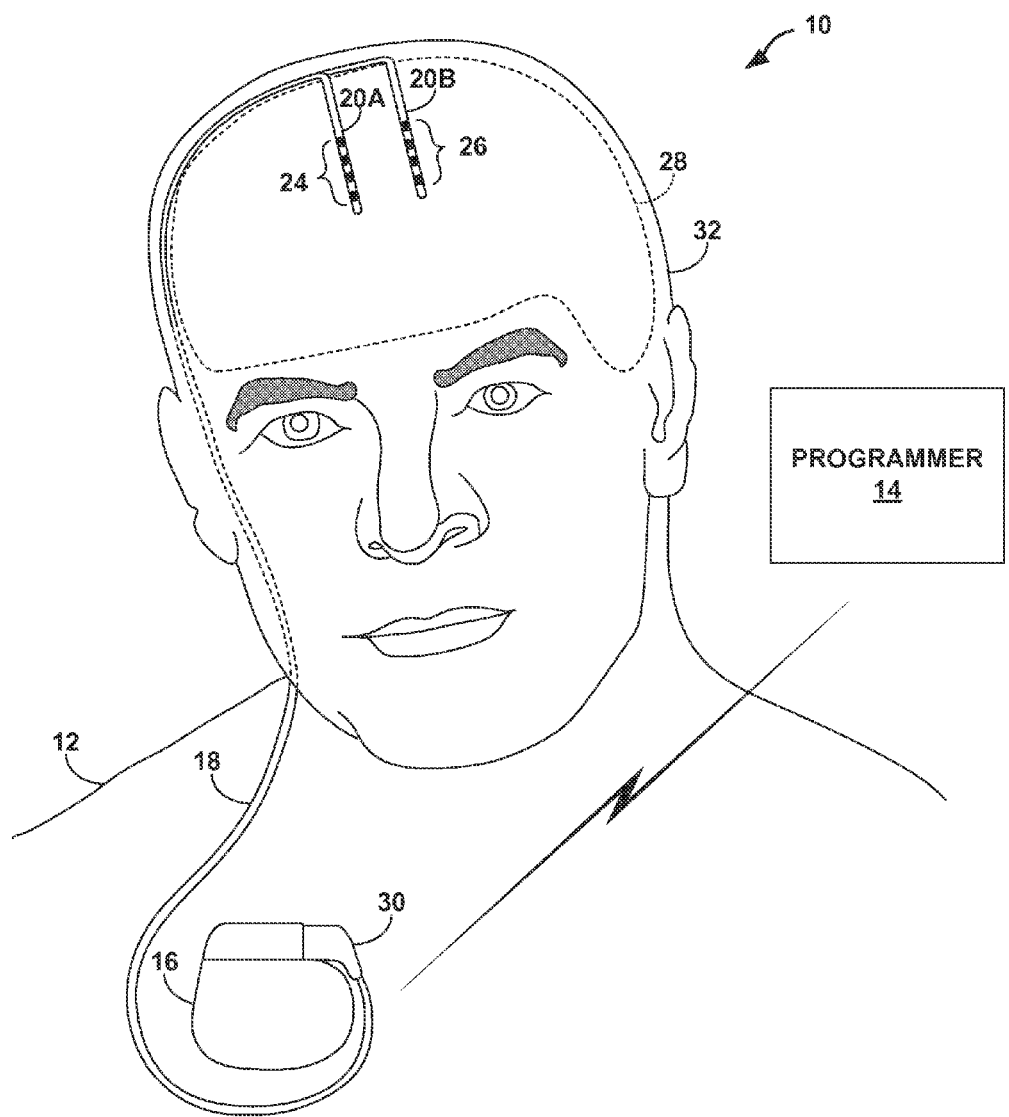
FIG. 1 is a conceptual diagram illustrating an example therapy delivery system.

Systems, devices, and techniques for delivering electrical stimulation via a medical device to the brain of a patient to modify the oscillation frequency of bioelectrical brain signals of the patient are described. In some examples, the bioelectrical brain signals may oscillate at a frequency that corresponds to pathological brain signals of the patient. When the biological brain signals of the patient oscillate at such a frequency, a medical device may deliver electrical stimulation (e.g., in the the form of pulses or continuous waveform) to the brain at a frequency selected to entrain the bioelectrical brain activity. When entrained, the frequency of the delivered electrical stimulation may then be adjusted to a different frequency to change the oscillation frequency of the bioelectrical brain signals of the patient. For example, the frequency of the delivered electrical stimulation may be adjusted to a frequency corresponding to non-pathological brain signals. In this manner, the bioelectrical brain signals of the patient may be modified via the delivered electrical stimulation from an oscillation frequency of pathological brain signals to an oscillation frequency of non-pathological brain signals.

As will be described further below, in some examples, electrical stimulation may be delivered by a medical device to the brain of the patient to manage or otherwise treat a patient disorder. In some examples, the oscillation of bioelectrical brain signals at a particular frequency or frequency band or range may be associated with one or more symptoms of a patient disorder. For example, bioelectrical brain signals oscillating in the particular frequency range may be associated with one or more symptoms of a patient disorder in the sense that such symptoms frequently occur or manifest themselves when the bioelectrical brain signals oscillate at such a frequency range. Such occurrences may be a result of the brain signal oscillations within one or more regions of the brain of a patient interfering with the normal function of that region of the brain. As used herein, a frequency or range of frequencies may be referred to as a pathological frequency or pathological frequency range when oscillations of brain signals at such frequency or frequencies are associated in such a manner with one or more symptoms of a patient disorder. Similarly, bioelectrical brain signals oscillating at one or more pathological frequencies may be referred to as pathological brain signals.

As one example, in the case of Parkinson's disease, beta frequency oscillations (e.g., between approximately 12 Hz to approximately 35 Hz) in the subthalamic nucleus (STN), globus pallidus interna ((GPi), globus pallidus externa (GPe), and/or other areas of the basal ganglia may be associated with one or more motor symptoms including, e.g., rigidity, akenesia, bradykinesia, diskensia, and/or resting tremor. These motor symptoms may be associated with bioelectrical brain signals oscillating in the beta frequency range in the sense that such symptoms frequently occur when the bioelectrical brain signals oscillate within the beta frequency range. For example, persistence of oscillation in the beta frequency range may result in oscillatory "interference" that can limit the normal functions of the above regions of the brain. Networks of oscillating neurons may be synchronized by electrical and chemical signals that cause the activity of the network to phase lock and resonate at some frequency. In some examples, the symptoms of Parkinson's disease generally manifest themselves in conjunction with the presence of beta frequency range oscillations (e.g., above some threshold activity level). In some examples, the frequency of symptom manifestations may increase in conjunction with the presence of beta frequency range oscillations.

In some examples, one or more symptoms of a patient disorder associated with oscillations of bioelectrical brain activity at a particular frequency or frequency band may be treated by reducing or substantially eliminating the oscillation of bioelectrical brain signals at such pathological frequencies when such activity occurs. For example, the manifestation of one or more symptoms associated with bioelectrical brain signals with oscillation in the beta frequency range for patients with Parkinson's disease may be reduced or substantially eliminated by modifying the bioelectrical brain signals to oscillate at one or more other frequencies outside the beta frequency range (e,g., within the gamma frequency band) that are not associated with the manifestation of such symptoms.

In accordance with some examples, electrical stimulation therapy may be delivered to the brain of a patient via a medical device to modulate the frequency at which bioelectrical brain signals of the patient oscillate. The electrical stimulation therapy may be delivered to the patient to adjust the bioelectrical brain signals of the patient from an oscillation frequency associated with symptoms of one or more patient disorders to another oscillation frequency (e.g., an oscillation frequency not associated with symptoms of one or more patient disorders). For example, electrical stimulation therapy may be delivered to the brain of a patient via a medical device to change the oscillation frequency of bioelectrical brain signals from pathological brain signals to non-pathological brain signals. In this manner, the electrical stimulation therapy may treat or otherwise manage a patient disorder by modulating the oscillation frequency of bioelectrical brain signals of the patient.

To modulate the bioelectrical brain signals, when bioelectrical brain signals are oscillating at a pathological frequency (which may refer to a frequency associated with the manifestation of one or more symptoms of a patient disorder), electrical stimulation therapy may be generated and delivered to the brain of a patient to entrain the bioelectrical brain signals. The bioelectrical brain signals may be characterized as being entrained by the delivered electrical stimulation when the bioelectrical brain signals when the bioelectrical brain signals may be pulled, drawn, or otherwise follow changes in the frequency of the delivered electrical stimulation. Entrainment may be the "following" of period and/or phase changes to delivered electrical stimulation for a period of time, and may include instances in which the changes of the bioelectrical brain signals are substantially the same as that of the changes to the delivered stimulation and instance in which the changes are not substantially the same but follow to some degree with the changes to the electrical stimulation. In some examples, entrainment of bioelectrical brain signals by the delivered electrical stimulation may be evidenced by an oscillation frequency of the brain signals that matches the frequency of the electrical stimulation and a constant phase relationship between the brain signal oscillations and the delivered electrical stimulation.

In some examples, the electrical stimulation may be delivered at substantially the same frequency as that of bioelectrical brain signal oscillations. In other examples, the electrical stimulation therapy may be delivered at some multiple (e.g., approximately 2 times, approximately 3 times, and/or approximately 0.5 times) of bioelectrical brain signal oscillations. By delivering electrical stimulation with a frequency that is substantially the same as that of the brain signal oscillation frequency or at substantially the same frequency of the oscillation times a whole integer (e.g., approximately 2 times, approximately 3 times, and so forth), the electrical stimulation delivered to the patient may have pulses (for stimulation including a plurality of pulses) or waveform peaks (for stimulation including a continuous waveform) to match substantially all peaks of the brain signal at the given oscillation frequency. In other examples, the stimulation frequency may be delivered at some frequency that is a fraction (½ or ¼, for example) of the brain signal oscillation frequency. In such a case, while pulses (for stimulation including a plurality of pulses) or waveform peaks (for stimulation including a continuous waveform) may not match substantially all peaks of the brain signal at the given oscillation frequency, the pulses (for stimulation including a plurality of pulses) or waveform peaks (for stimulation including a continuous waveform) may match a fraction of the peaks of the brain signal (e.g., approximately 50 percent for stimulation at a frequency approximately one half of the oscillation frequency). In some example, the frequency of the brain signals may be at least approximately 0.25, such as, at least approximately 0.5 times that of the brain signal oscillation frequency.

As will be described further below, when the bioelectrical brain signals are entrained by the delivered electrical stimulation therapy, the frequency of the electrical stimulation delivered to the brain of the patient via the medical device may be adjusted (e.g., increased or decreased). Since the bioelectrical brain signals are entrained with the delivered electrical stimulation, the oscillation frequency of the bioelectrical brain signals may follow in kind with the adjustment to the frequency of the electrical stimulation therapy. For example, if the frequency of the electrical stimulation therapy is increased, the oscillation frequency of the bioelectrical brain signals may also increase. Similarly, if the frequency of the electrical stimulation therapy is decreased, the oscillation frequency of the bioelectrical brain signals may also decrease. In some examples, the increase/decrease in the oscillation frequency may be directly proportional (e.g., approximately one to one) with the increase/decrease in the frequency of the electrical stimulation therapy delivered to the brain of the patient via the medical device. In other examples, the degree of increase/decrease in the oscillation frequency may not be directly proportional with the increase/decrease in the frequency of the electrical stimulation therapy delivered to the brain of the patient via the medical device. For example, the increase or decrease in the oscillation frequency may be less than the increase or decrease, respectfully, in the frequency of the electrical stimulation therapy delivered to the brain of the patient via the medical device To treat or otherwise manage a patient disorder, the frequency adjustment to the delivered electrical stimulation may cause the oscillation frequency to change from the pathological frequency. For example, the frequency of the electrical stimulation may be adjusted to modulate the oscillation frequency of the bioelectrical brain signals to a target frequency that is associated with non-pathological brain activity or some other frequency associated with reduced manifestations of one or more symptoms of the patient disorder. The frequency of the delivered electrical stimulation may be adjusted by sweeping and/or stepping the frequency from the oscillation frequency of the bioelectrical brain signal to the target frequency. When initiated, the frequency of the electrical stimulation may be delivered at a frequency selected to entrain the bioelectrical brain signals, or the frequency of the electrical stimulation may be adjusted to such a frequency from the initial frequency (e.g., by sweeping or stepping the frequency to a frequency selected to entrain the bioelectrical brain signals).

In some examples, such electrical stimulation therapy may be delivered to the brain of the patient upon detecting the bioelectrical brain signal oscillations at a pathological frequency and/or the detection of manifestations of one or more motor symptoms associated with the pathological frequency. Additionally or alternatively, such electrical stimulation therapy may be periodically delivered to the brain of a patient and not in response to the detection of oscillations at a pathological frequency and/or the detection of manifestations of one or more motor symptoms associated with the pathological frequency. In some examples, the electrical stimulation therapy may be delivered in response to patient input. In some examples, the electrical stimulation may be continuously delivered to the patient.

FIG. 1 is a conceptual diagram illustrating an example therapy system 10 in accordance with examples of the disclosure. In FIG. 1, example therapy system 10 may deliver electrical stimulation therapy to treat or otherwise manage a patient condition, such as, e.g., a movement disorder of patient 12. One example of a movement disorder treated by the delivery of DBS via system 10 may include Parkinson's disease. Patient 12 ordinarily will be a human patient. In some cases, however, therapy system 10 may be applied to other mammalian or non-mammalian non-human patients.

For ease of illustration, examples of the disclosure will primarily be described with regard to the treatment of movement disorders and, in particular, the treatment of Parkinson's disease, e.g., by reducing or preventing the manifestation of symptoms exhibited by patients suffering from Parkinson's disease. As noted above, such symptoms may include rigidity, akenesia, bradykinesia, diskensia, and/or resting tremor. However, the treatment of one or more patient disorders other than that of Parkinson's disease by employing the techniques described herein are contemplated. For example, the described techniques may be employed to manage or other treat symptoms of other patient disorders, such as, but not limited to, psychological disorders, mood disorders, seizure disorders or other neurogenerative impairment. In one example, such techniques may be employed to provide therapy to patient to manage Alzheimer's disease.

Therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation therapy module that includes a stimulation generator that generates and delivers electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28).

In some examples, delivery of stimulation to one or more regions of brain 28, such as an anterior nucleus (AN), thalamus or cortex of brain 28, provides an effective treatment to manage a disorder of patient 12. In some examples, IMD 16 may provide cortical stimulation therapy to patient 12, e.g., by delivering electrical stimulation to one or more tissue sites in the cortex of brain 28. In cases in which IMD 16 delivers electrical stimulation to brain 28 to treat Parkinson's disease by modulating brain signals oscillating at pathological frequencies, target stimulation sites may include one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex. Brain signals with oscillations in the beta frequency range may be considered pathological brain signals. As will be described below, IMD 16 may deliver electrical stimulation selected to entrain the bioetectrical brain signals oscillating in the beta frequency range and adjust the frequency of the electrical stimulation to change the oscillation frequency to a higher or lower frequency, e.g., a frequency greater than approximately 40 Hz, such as, e.g., between approximately 40 Hz and approximately 100 Hz or up to approximately 350 Hz. For instances in which IMD 16 senses the bioelectrical brain signals at one or more sites of brain 28 to detection oscillations at a pathological frequency, the target stimulation site(s) for electrical stimulation delivered to brain 28 of patient 28 may be the same and/or different than the sensing site.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. Generally, IMD 16 is constructed of a biocompatible material that resists corrosion and degradation from bodily fluids. IMD 16 may comprise a hermetic housing 34 to substantially enclose components, such as a processor, therapy module, and memory.

Leads 20A and 20B may be implanted within the right and left hemispheres, respectively, of brain 28 in order deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment, For example, in the case of Parkinson's disease, for example, leads 20 may be implanted to deliver electrical stimulation to one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may deliver electrical stimulation to treat any number of neurological disorders or diseases in addition to movement disorders, such as seizure disorders or psychiatric disorders. Examples of movement disorders include a reduction in muscle control, motion impairment or other movement problems, such as rigidity, bradykinesia, rhythmic hyperkinesia, nonrhythmic hyperkinesia, dystonia, tremor, and akinesia. Movement disorders may be associated with patient disease states, such as Parkinson's disease or Huntington's disease. Examples of psychiatric disorders include MDD, bipolar disorder, anxiety disorders, post traumatic stress disorder, dysthymic disorder, and OCD. As described above, while examples of the disclosure are primarily described with regard to treating Parkinson's disease, treatment of other patient disorders via delivery of therapy to brain 28 is contemplated.

Leads 20 may be implanted within a desired location of brain 28 via any suitable technique, such as through respective burr holes in a skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help prevent the onset of events associated with the patient's disorder or mitigate symptoms of the disorder. For example, electrical stimulation delivered by IMD 16 to a target tissue site within brain 28 may have a frequency (and/or other stimulation parameter values) selected to entrain bioelectrical brain signals oscillating at a pathological frequency. The frequency of the electrical stimulation may then be adjusted such that the oscillation frequency of the entrained bioelectrical brain signals change to a frequency other than of the pathological frequency. In this manner, IMD 16 may deliver electrical stimulation to reduce or prevent the onset of events associated with the patient's disorder or mitigate symptoms of the disorder.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields. The complex electrode array geometry may include multiple electrodes (e.g., partial ring or segmented electrodes) around the perimeter of each lead 20, rather than a ring electrode. In this manner, electrical stimulation may be directed to a specific direction from leads 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In alternative examples, leads 20 may have shapes other than elongated cylinders as shown in FIG. 1. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs, A therapy program may define one or more electrical stimulation parameter values for therapy generated and delivered from IMD 16 to brain 28 of patient 12. Where IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 12, therapy system 10 monitors one or more bioelectrical brain signals of patient 12. For example, IMD 16 may include a sensing module that senses bioelectrical brain signals within one or more regions of brain 28. In the example shown in FIG. 1, the signals generated by electrodes 24, 26 are conducted to the sensing module within IMD 16 via conductors within the respective lead 20A, 20B. As described in further detail below, in some examples, a processor of IMD 16 may sense the bioelectrical signals within brain 28 of patient 12 and controls delivery of electrical stimulation therapy to brain 28 via electrodes 24, 26 when the bioelectrical brain signals are oscillating at a pathological frequency.

In some examples, the sensing module of IMD 16 may receive the bioelectrical signals from electrodes 24, 26 or other electrodes positioned to monitored brain signals of patient 12. Electrodes 24, 26 may also be used to deliver electrical stimulation from the therapy module to target sites within brain 28 as well as sense brain signals within brain 28. However, IMD 16 can also use separate sensing electrodes to sense the bioelectrical brain signals. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

Depending on the particular stimulation electrodes and sense electrodes used by IMD 16, IMD 16 may monitor brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a brain signal of patient 12 may be monitored with external electrodes, e.g., scalp electrodes. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical brain signals monitored by IMD 16 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LFP) sensed from within one or more regions of a patient's brain and/or action potentials from single cells within the patient's brain.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may provide efficacious therapy to patient 12 to address symptoms associated with the seizure disorder (or other patient condition). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient (e.g., heart rate, respiratory rate or muscle activity). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Figure 2:
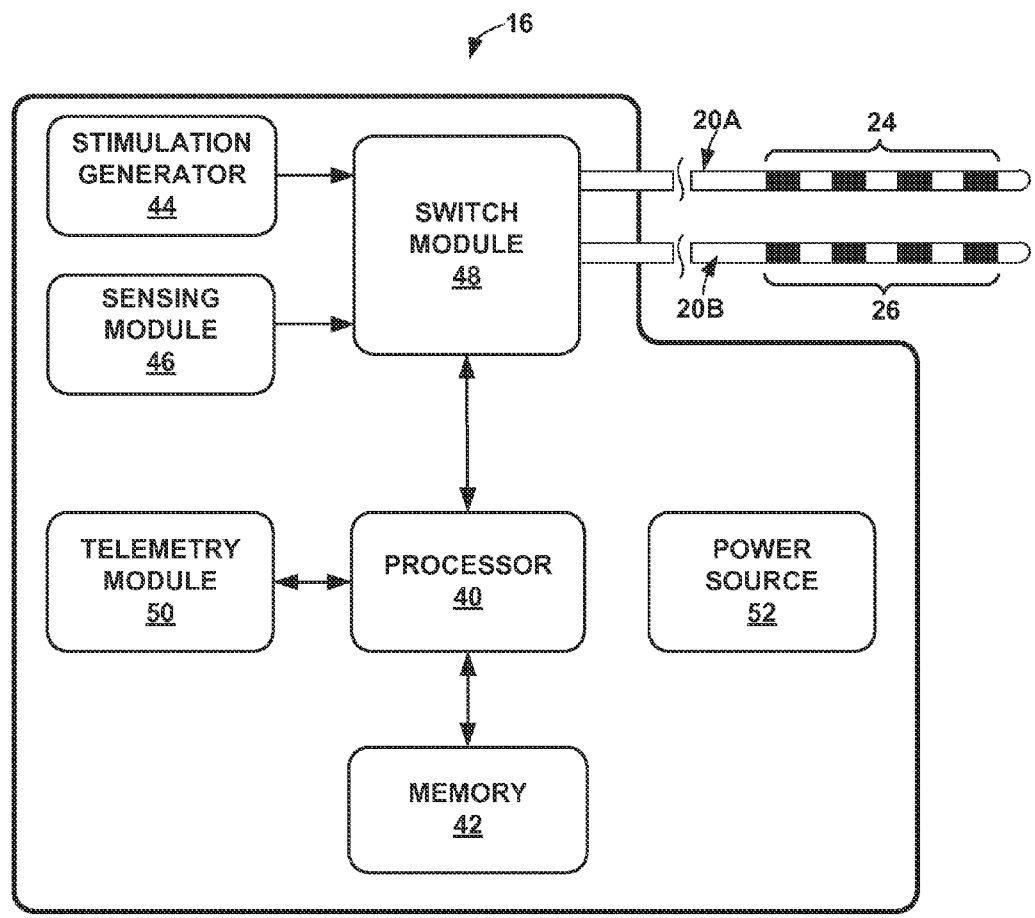
FIG. 2 is functional block diagram illustrating components of an example medical device.

FIG. 2 is a functional block diagram illustrating components of an example IMD 16. In the example shown in FIG. 2, IMD 16 includes memory 40, processor 42, stimulation generator 44, sensing module 46, switch module 48, telemetry module 50, and power source 52. Processor 42 may include any one or more microprocessors, controllers, digital signal processors (DSPs), application specific integrated circuits (ASICs), field-programmable gate arrays (FPGAs), and discrete logic circuitry. The functions attributed to processors described herein, including processor 42, may be provided by a hardware device and embodied as software, firmware, hardware, or any combination thereof.

In the example shown in FIG. 2, sensing module 46 senses bioelectrical brain signals of patient 12 via select combinations of electrodes 24, 26. Sensing module 46 may include circuitry that measures the electrical activity of a particular region, e.g., an anterior nucleus, thalamus or cortex of brain 24 via select electrodes 24, 26. For treatment of Parkinson's disease, sensing module 46 may be configured to measure the electrical activity of the subthalamic nucleus (STN), globus pallidus interna (GPi), globus pallidus externa (GPe), and/or other areas of the basal ganglia.

Sensing module 46 may sample the bioelectrical brain signal substantially continuously or at regular intervals, such as, but not limited to, a frequency of about 1 Hz to about 1000 Hz, such as about 250 Hz to about 1000 Hz or about 500 Hz to about 1000 Hz. Sensing module 46 includes circuitry for determining a voltage difference between two electrodes 24, 26, which generally indicates the electrical activity within the particular region of brain 24. One of the electrodes 26, 24 may act as a reference electrode, and, if sensing module 46 is implanted within patient 12, a housing of IMD 16 or the sensing module in examples in which sensing module 46 is separate from IMD 16, may include one or more electrodes that may be used to sense bioelectrical brain signals.

The output of sensing module 46 may be received by processor 42. In some cases, processor 42 may apply additional processing to the bioelectrical signals, e.g., convert the output to digital values for processing and/or amplify the bioelectrical brain signal. In addition, in some examples, sensing module 46 or processor 42 may filter the signal from the selected electrodes 24, 26 in order to remove undesirable artifacts from the signal, such as noise from cardiac signals generated within the body of patient 12. Although sensing module 46 is incorporated into a common outer housing with stimulation generator 44 and processor 42 in FIG. 2, in other examples, sensing module 46 is in a separate outer housing from the outer housing of IMD 16 and communicates with processor 42 via wired or wireless communication techniques. In other examples, a bioelectrical brain signal may be sensed via external electrodes (e.g., scalp electrodes).

In some examples, sensing module 46 may include circuitry to tune to and extract a power level of a particular frequency band of a sensed brain signal. Thus, the power level of a particular frequency band of a sensed brain signal may be extracted prior to digitization of the signal by processor 34. By tuning to and extracting the power level of a particular frequency band before the signal is digitized, it may be possible to run frequency domain analysis algorithms at a relatively slower rate compared to systems that do not include a circuit to extract a power level of a particular frequency band of a sensed brain signal prior to digitization of the signal. In some examples, sensing module 46 may include more than one channel to monitor simultaneous activity in different frequency bands, i.e., to extract the power level of more than one frequency band of a sensed brain signal. These frequency bands may include an alpha frequency band (e.g., 8 Hz to 12 Hz, beta frequency band (e.g., approximately 12 Hz to approximately 35 Hz), gamma frequency band (e.g., between approximately 35 Hz to approximately 200 Hz), or other frequency bands.

In some examples, sensing module 26 may include an architecture that merges chopper-stabilization with heterodyne signal processing to support a low-noise amplifier. In some examples, sensing module 26 may include a frequency selective signal monitor that includes a chopper-stabilized superheterodyne instrumentation amplifier and a signal analysis unit. Example amplifiers that may be included in the frequency selective signal monitor are described in further detail in commonly-assigned U.S. Patent Publication No. 2009/0082691 to Denison et al., entitled, "FREQUENCY SELECTIVE MONITORING OF PHYSIOLOGICAL SIGNALS" and filed on Sep. 25, 2008. U.S. Patent Publication No. 2009/0082691 to Denison et al. is incorporated herein by reference in its entirety.

As described in U.S. Patent Publication No. 2009/0082691 to Denison et al., frequency selective signal monitor may utilize a heterodyning, chopper-stabilized amplifier architecture to convert a selected frequency band of a physiological signal to a baseband for analysis. The physiological signal may include a bioelectrical brain signal, which may be analyzed in one or more selected frequency bands to detect bioelectrical brain signals oscillating at a pathological frequency and, in response, deliver electrical stimulation to modulate the oscillating frequency of the bioelectrical brain signals in accordance with some of the techniques described herein. The frequency selective signal monitor may provide a physiological signal monitoring device comprising a physiological sensing element that receives a physiological signal, an instrumentation amplifier comprising a modulator that modulates the signal at a first frequency, an amplifier that amplifies the modulated signal, and a demodulator that demodulates the amplified signal at a second frequency different from the first frequency. A signal analysis unit may analyze a characteristic of the signal in the selected frequency band. The second frequency may be selected such that the demodulator substantially centers a selected frequency band of the signal at a baseband.

In some examples, sensing module 46 may sense brain signals substantially at the same time that IMD 16 delivers therapy to patient 14. In other examples, sensing module 46 may sense brain signals and IMD 16 may deliver therapy at different times.

In some examples, sensing module 46 may monitor one or more physiological parameters of a patient other than that of bioelectrical brain signals, which are indicative of a patient disorder, e.g., in combination with the monitored bioelectrical brains signals of the patients. Suitable patient physiological parameters may include, but are not limited to, muscle tone (e.g., as sensed via electromyography (EMG)), eye movement (e.g., as sensed via electroculography (EOG) or EEG), and body temperature. In some examples, patient movement may be monitored via actigraphy. In one example, processor 40 may monitor an EMG signal reflective of the muscle tone of patient 12 to identify physical movement of the patient. Alternatively or additionally, processor 40 may monitor the physical movement of a patient via one or more motion sensors, such as, e.g., one or more single or multi-axis accelerometer devices.

In some examples, sensing module 46 may monitor one or more physiological parameters of a patient other than that of bioelectrical brain signals, which are indicative of symptoms of Parkinson's disease. For examples, sensing module 46 may monitor one or more parameters indicative of muscle stiffness or movement (slow movement, tremor, and lack of movement) with may correspond to one or more symptoms of Parkinson's disease. Such parameters may be detected by EMG signals, actigraphy, accelerometers signals, and/or other suitable signal. In some examples, in response to the detection of one or more symptoms of Parkinson's disease based on the monitoring of such parameter(s), IMD 16 may deliver electrical stimulation selected to entrain brain signals oscillating at a frequency associated with the detected symptoms, and then adjust the frequency to change the oscillation frequency of the brain signals to a frequency not associated with the detected symptoms.

Memory 40 may include any volatile or non-volatile media, such as a random access memory (RAM), read only memory (ROM), non-volatile RAM (NVRAM), electrically erasable programmable ROM (EEPROM), flash memory, and the like. Memory 40 may store computer-readable instructions that, when executed by processor 42, cause IMD 16 to perform various functions described herein. Memory 40 may be considered, in some examples, a non-transitory computer-readable storage medium comprising instructions that cause one or more processors, such as, e.g., processor 42, to implement one or more of the example techniques described in this disclosure. The term "non-transitory" may indicate that the storage medium is not embodied in a carrier wave or a propagated signal. However, the term "non-transitory" should not be interpreted to mean that memory 40 is non-movable. As one example, memory 40 may be removed from IMD 16, and moved to another device. In certain examples, a non-transitory storage medium may store data that can, over time, change (e.g., in RAM).

In the example shown in FIG. 2, the set of electrodes 24 of lead 20A includes four electrodes, and the set of electrodes 26 of lead 20B includes four electrodes. Processor 42 controls switch module 48 to sense bioelectrical brain signals with selected combinations of electrodes 24, 26. In particular, switch module 48 may create or cut off electrical connections between sensing module 46 and selected electrodes 24, 26 in order to selectively sense bioelectrical brain signals, e.g., in particular portions of brain 28 of patient 12. Processor 42 may also control switch module 48 to apply stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 22A, 22B and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48. In some examples, IMD 16 may include separate current sources and sinks for each individual electrode (e.g., instead of a single stimulation generator) such that switch module 48 may not be necessary.

Stimulation generator 44 may be a single channel or multi-channel stimulation generator. For example, stimulation generator 44 may be capable of delivering, a single stimulation pulse, multiple stimulation pulses or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

In accordance with one or more examples of the disclosure, processor 40 and/or a processor of another device (e.g., a processor of external programmer 14) may control stimulation generator 44 to generate and deliver electrical stimulation to one or more regions of brain 28 to modulate the oscillation frequency of bioelectrical brain signals in one or more regions of brain 28. For example, when bioelectrical brain signals are oscillating at a pathological frequency within a region of brain 28, processor 40 may control stimulation generator 44 to generate and deliver electrical stimulation to the region of brain 28 at a frequency selected to entrain the bioelectrical brain signals oscillating at the pathological frequency. Processor 40 may then adjust the frequency of the delivered electrical stimulation therapy (e.g., increase or decrease) to change the oscillation frequency of the entrained bioelectrical brain signals.

In some examples, processor 40 may adjust the frequency of the delivered electrical stimulation such that the oscillation frequency of the pathological brain signals change from that of a pathological frequency to another frequency. For example, the adjustment to the frequency of the delivered electrical stimulation may cause the oscillation frequency of the bioelectrical brain signals to change from a pathological frequency to a non-pathological frequency. The change to the oscillation frequency may result in a reduction or elimination of one or more symptoms of a patient disorder associated with the pathological frequency.

Telemetry module 50 may support wireless communication between IMD 16 and an external programmer 14 or another computing device under the control of processor 42. Processor 42 of IMD 16 may, for example, transmit bioelectrical brain signals, seizure probability metrics for particular sleep stages, a seizure probability profile for patient 12, and the like via telemetry module 50 to a telemetry module within programmer 14 or another external device. Telemetry module 50 in IMD 16, as well as telemetry modules in other devices and systems described herein, such as programmer 14, may accomplish communication by radiofrequency (RF) communication techniques. In addition, telemetry module 50 may communicate with external programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
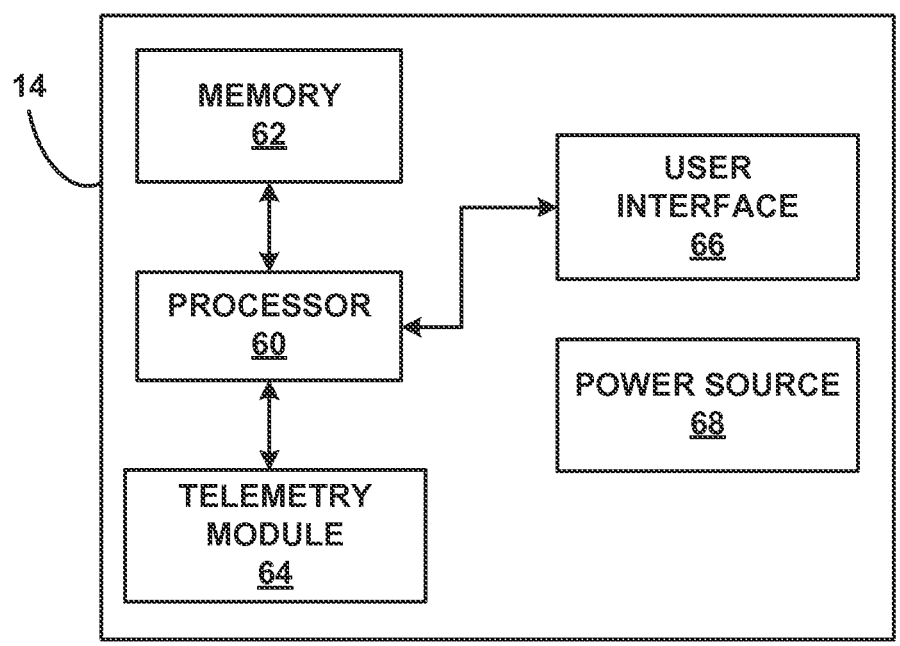
FIG. 3 is a functional block diagram illustrating components of an example medical device programmer.

FIG. 3 is a conceptual block diagram of an example external medical device programmer 14, which includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 14 through user interface 66. User interface 66 includes a display (not shown), such as a LCD or LED display or other type of screen, to present information related to treatment of the seizure disorder of patient 12. User interface 66 may also include an input mechanism to receive input from the user. The input mechanisms may include, for example, buttons, a keypad (e.g., an alphanumeric keypad), a peripheral pointing device or another input mechanism that allows the user to navigate though user interfaces presented by processor 60 of programmer 14 and provide input.

Memory 62 may include instructions for operating user interface 66 and telemetry module 64, and for managing power source 68. Memory 62 may also store any therapy data retrieved from IMD 16 during the course of therapy, as well as sensed bioelectrical brain signals. The clinician may use this therapy data to determine the progression of the patient condition in order to plan future treatment. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Memory 62 may be considered, in some examples, a non-transitory computer-readable storage medium comprising instructions that cause one or more processors, such as, e.g., processor 60, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable. As one example, memory 62 may be removed from programmer 14, and moved to another device. In certain examples, a non-transitory storage medium may store data that can, over time, change (e.g., in RAM).

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 may deliver operating power to the components of programmer 14. Power source 68 may include a battery and a power generation circuit to produce the operating power. In some examples, the battery may be rechargeable to allow extended operation.

Figure 4:
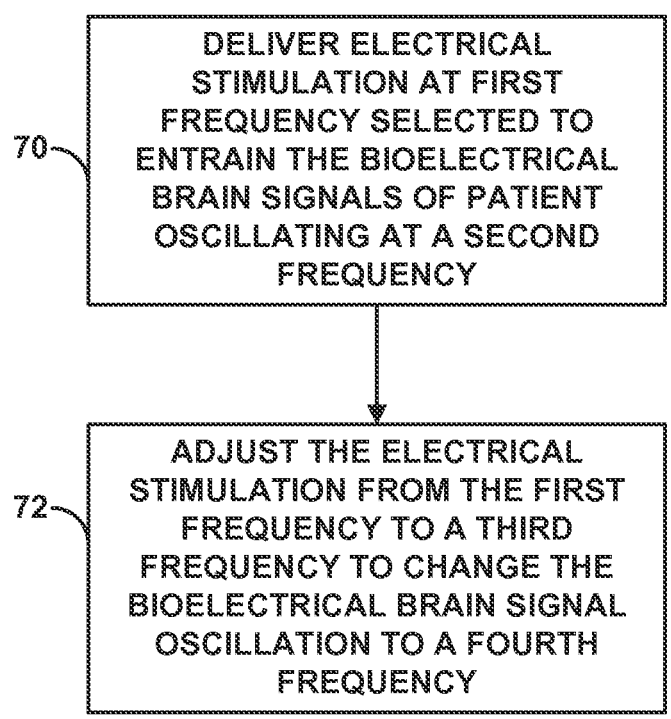
FIG. 4 is a flow diagram illustrating an example technique for delivering electrical stimulation therapy to the brain of a patient.
Figure 5:
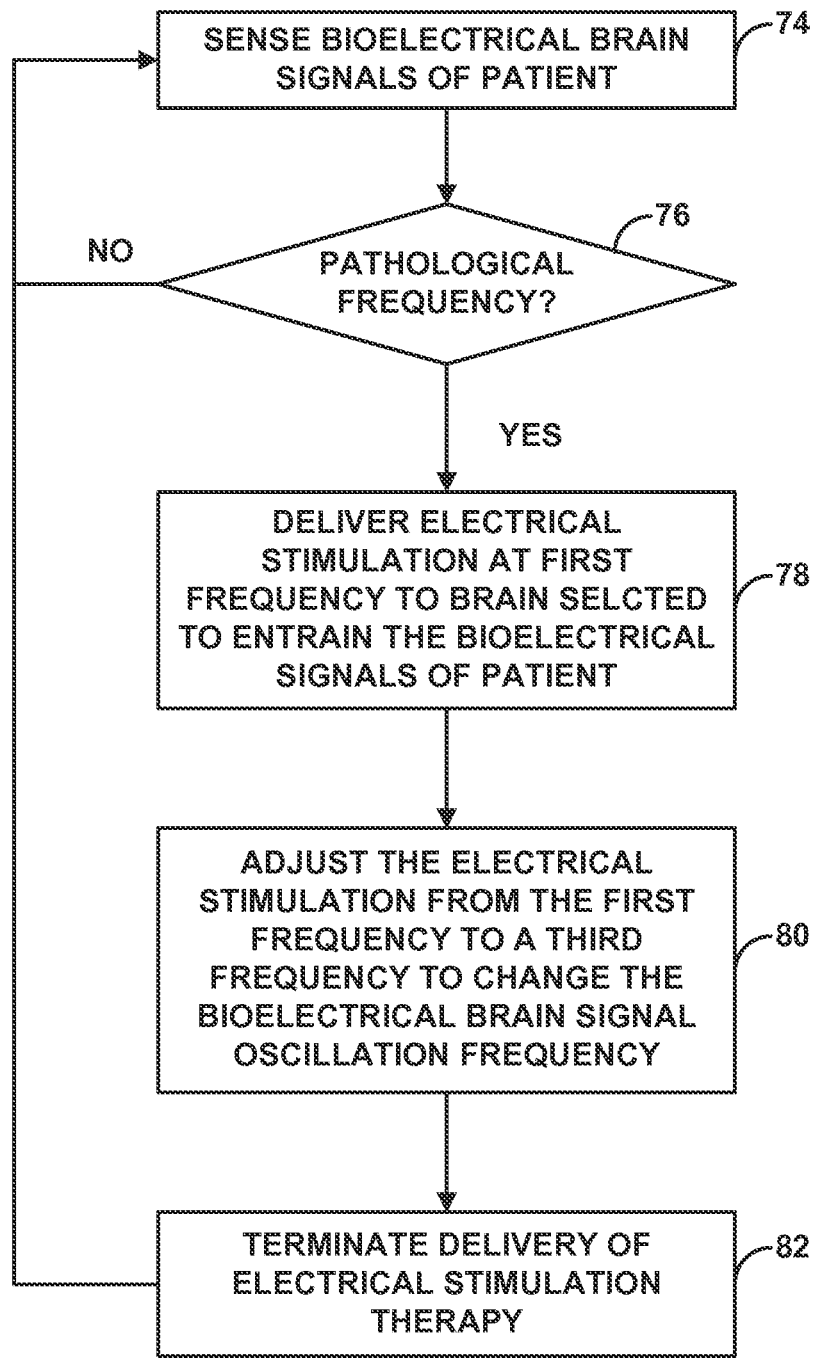
FIG. 5 is a flow diagram illustrating another example technique for delivering electrical stimulation therapy to the brain of a patient.

FIGS. 4 and 5 are flow diagrams illustrating two example techniques for modulating bioelectrical brain signals of patient 12 via the delivery of electrical stimulation therapy. For ease of illustration, the example of FIGS. 4 and 5 are described with regard to therapy system 10. However, the same or substantially similar techniques may be employed in any suitable systems or devices capable of delivering electrical stimulation to the brain of patient 12. Also, as described above, while the example techniques of FIGS. 4 and 5 are described with regard to the treatment of Parkinson's disease by modulating bioelectrical brain signals with oscillation frequencies associated with one or more motor symptoms of Parkinson's disease, such techniques may be employed to treat patient disorders other than that of Parkinson's disease.

As shown in FIG. 4, to modulate or otherwise change the oscillation frequency of bioelectrical brain signals oscillating at a second frequency at one or more regions of brain 28, processor 40 of IMD 16 may control stimulation generator 44 to generate and deliver electrical stimulation at a first frequency to brain 28 via one or more of electrodes 24, 26, where the first frequency (in addition to other stimulation parameter values) may be selected to entrain the bioelectrical brain signals (70). As noted above, the electrical stimulation may be delivered in the form of electrical stimulation pulses and/or a continuous waveform.

When the bioelectrical brain signals oscillating at the second frequency are entrained by the electrical stimulation delivered by IMD 16, processor 40 may control stimulation generator 44 to adjust the frequency of the electrical stimulation to a third frequency to change the oscillation frequency of the bioelectrical brain signals to a fourth frequency (72). The third frequency may be greater than or less than the first frequency used to entrain the bioelectrical brain signals oscillating at the second frequency. The third frequency may also be greater than or less than the second frequency of the pathological brain signals. Due to the entrainment of the bioelectrical brain signals by the delivered electrical stimulation, the adjustment to the electrical stimulation delivered to one or more regions of brain 28 of patient 12 may change the oscillation frequency of the bioelectrical brain signals to a fourth frequency from that of the second frequency. For example, the adjustment of the electrical stimulation from the first frequency to the third frequency may cause the bioelectrical brain signals to oscillate at fourth frequency that is the same or substantially similar to that of the third frequency (72). In some examples, the fourth frequency may correspond to an oscillation frequency that corresponds to non-pathological brain signals, and may be the same or different than that of the third frequency of the adjusted electrical stimulation.

The example of FIG. 4 may be used to treat or otherwise manage a patient disorder by reducing or substantially eliminating manifestations of the disorder associated with certain types of bioelectrical brain signals. For example, the oscillation of bioelectrical brain signals at the second frequency may correspond to pathological brain signals in the sense that the oscillation of the brain signals at the second frequency are associated with the manifestation of one or more symptoms or undesired effects of the patient disorder. Pathological brain signal frequencies may be specific to one or more regions of brain 28, and may be patient and/or disorder specific.

For example, for Parkinson's disease, the second frequency in the example of FIG. 4 may generally correspond to one more oscillation frequencies with beta band (between approximately 12 Hz to approximately 35 Hz). As described above, in the case of Parkinson's disease, beta frequency oscillations in the subthalamic nucleus (STN), globus pallidus interna (GPi), globus pallidus externa (GPe), and/or other areas of the basal ganglia may be associated with one or more motor symptoms including, e.g., rigidity, akenesia, bradykinesia, diskensia, and/or resting tremor. These motor symptoms may be associated with bioelectrical brain signals oscillating in the beta frequency range in the sense that such symptoms frequently occur when the bioelectrical brain signals within the above regions of brain 28 oscillate within the beta frequency range. While beta frequency oscillations may be present in some degree in many patients, Parkinson's patients may display an exaggerated presence of beta frequency oscillations that are associated with one or more symptom manifestations. In some examples, indicators such as oscillatory activity (e.g., signal energy) may be quantified in terms of measured local field potential power, or may be quantified as a relative power (e.g., as a percentage of signal power within a given frequency band to the overall signal power), using fast fourier transform (FFT) techniques, for example, or beta burst may be used as indicators of pathological brain. Regardless of how the pathological brain signals are identified, by changing the oscillation frequency of the bioelectrical brain signals within one or more of the above regions from the second frequency to a fourth frequency (e.g., a frequency outside the beta frequency band and/or a non-pathological frequency), motor symptoms that manifest themselves when beta frequency oscillations are present may be reduced or substantially eliminated using the example technique of FIG. 4.

In the example of FIG. 4, processor 40 may generally control the delivery of electrical stimulation in a manner that entrains the bioelectrical brain signals oscillating at the second frequency. The bioelectrical brain signals may be characterized at being entrained by the delivered electrical stimulation when the bioelectrical brain signals when the bioelectrical brain signals may be pulled, drawn, or otherwise follow changes in the frequency of the delivered electrical stimulation. Entrainment may be the "following" of period and/or phase changes to delivered electrical stimulation for a period of time, and may include instance in which the changes the bioelectrical brain signals are substantially the same as that of the changes to the delivered stimulation and instance in which the changes are not substantially the same but follow to some degree with the changes to the electrical stimulation. In some examples, entrainment of bioelectrical brain signals oscillating at the second frequency by the electrical stimulation delivered at the first frequency may be evidenced by an oscillation frequency of the brain signals that matches the frequency of the electrical stimulation and a constant phase relationship between the brain signal oscillations and the delivered electrical stimulation.

The entrainment of the bioelectrical brain signals by the delivered electrical stimulation may be depend on a number of variables, which may include the stimulation frequency relative the oscillation frequency of the bioelectrical brain signals, the length of time that the electrical stimulation is delivered at the specified frequency, and/or the target tissue site of brain 28 that the electrical stimulation is delivered.

For example, the first frequency of the electrical stimulation delivered to brain 28 of patient 12 may be selected to entrain the bioelectrical brain signals oscillating at the second frequency. In some examples, the first frequency may be substantially the same as the second frequency. In some examples, the first frequency may be within approximately 10 percent of the second frequency. In other examples, the first frequency of the delivered electrical stimulation may be some multiple (approximately 2 times, 3 times, and/or 0.5 times) of bioelectrical brain signals oscillations. By delivering electrical stimulation with a frequency that is substantially the same as that of the brain signal oscillation frequency or at substantially the same frequency of the oscillation time a whole integer (e.g., approximately 2 times, approximately 3 times, and so forth), the electrical stimulation delivered to the patient may have pulses (for stimulation including a plurality of pulses) or waveform peaks (for stimulation including a continuous waveform) to match substantially all peaks of the brain signal at the given oscillation frequency. In other examples, the stimulation frequency may be delivered at some frequency that is a fraction (½ or ¼, for example) of the brain signal oscillation frequency. In such a case, while pulses (for stimulation including a plurality of pulses) or waveform peaks (for stimulation including a continuous waveform) may not match substantially all peaks of the brain signal at the given oscillation frequency, the pulses (for stimulation including a plurality of pulses) or waveform peaks (for stimulation including a continuous waveform) may match a fraction of the peaks of the brain signal (e.g., approximately 50 percent for stimulation at a frequency approximately one half of the oscillation frequency). In some example, the frequency of the brain signals may be at least approximately 0.25, such as, at least approximately 0.5 times that of the brain signal oscillation frequency.

In addition to the frequency of the delivered electrical stimulation, processor 40 may control the values of the other stimulation parameters (e.g., amplitude, pulse width) such that the stimulation entrains the brain signals of the patient. For example, processor 40 may control the delivery of stimulation to have an amplitude (pulse or waveform) at the therapeutic level, which may be greater than the amplitude of the brain signal oscillations. In some examples, the amplitude of the stimulation may be between approximately 0.5 volts and approximately 10 volts, such as, e.g., between approximately 0.5 volts and approximately 5 volts, between approximately 0.5 volts and approximately 5 volts, or between approximately 0.5 volts and approximately 2 volts. Other values are contemplated.

Additionally or alternatively, the amount of time at which processor 40 may control the delivery of electrical stimulation to brain 28 of patient 12 at the first frequency prior to adjusting the frequency of the electrical stimulation may be selected to entrain the bioelectrical brain signals oscillating at the second frequency. In some examples, IMD 16 may deliver the electrical stimulation at the first frequency to brain 28 to entrain the bioelectrical brain signals oscillating at the second frequency for between approximately 50 milliseconds and approximately 5000 milliseconds, such as, e.g., between approximately 300 milliseconds and approximately 1500 milliseconds. In some examples, IMD 16 may deliver the electrical stimulation at the first frequency to brain 28 to entrain the bioelectrical brain signals oscillating at the second frequency for at least approximately 50 millisecond, e.g., for at least 300 milliseconds. In some examples, IMD 16 may deliver the electrical stimulation at the first frequency to brain 28 for at least a length of time approximately equal to at least two periods (e.g., at least three cycles) of the brain signal at the oscillation frequency to be entrained, such that the length of time for delivering the stimulation varies based on the oscillation frequency of the brain signals to be entrained.

Additionally or alternatively, the target tissue site at which processor 40 may control the delivery of electrical stimulation to brain 28 of patient 12 at the first frequency prior to adjusting the frequency of the electrical stimulation may be selected to entrain the bioelectrical brain signals oscillating at the second frequency. In some examples, IMD 16 may deliver the electrical stimulation to substantially the same region or regions in which the bioelectrical brain signals oscillating at the second frequency are exhibited. For examples in which IMD 16 senses the bioelectrical brain signals of patient 12 via sensing module 46, IMD 16 may deliver the electrical stimulation to brain 28 of patient using one or more of electrodes 24, 26 used to sense the bioelectrical brain signals. In some examples, IMD 16 may deliver the electrical stimulation to one or more different regions of brain 28 than the one or more regions in which the bioelectrical brain signals oscillating at the second frequency are exhibited.

When the bioelectrical brain signals oscillating at the second frequency are entrained by the electrical stimulation delivered at the first frequency, the oscillation frequency of the entrained bioelectrical brain signals may change or follow in kind with changes to the frequency of the electrical stimulation. For example, with regard to the example of FIG. 4, if the adjustment from the first frequency to the third frequency is an increase in frequency, the oscillation frequency of the bioelectrical brain signals may also increase. Conversely, if the adjustment from the first frequency to the third frequency is a decrease in frequency, the oscillation frequency of the bioelectrical brain signals may also decrease. In each case, the change to the oscillation frequency of the bioelectrical brain signals may be substantially synchronized with the adjustment to the frequency of the electrical stimulation or after some nominal time delay.

In some examples, IMD 16 may be configured to check or otherwise verify that the brain signals have been entrained by the delivered stimulation. For example, in some cases, IMD 16 may sense the brain signals via electrodes 24, 26 while the electrical stimulation is adjusted (e.g., to a non-pathological frequency) to determined whether or not the brain signal oscillation frequency is following the frequency of the stimulation. Additionally or alternatively, IMD 16 may be configured to deliver electrical stimulation at a frequency slightly above or below that of the brain signal oscillation frequency. For example, for brain signals oscillating at 30 Hz, IMD 16 may deliver electrical stimulation at a frequency of 32 Hz and hold the frequency substantially constant for a period of time. IMD 16 may monitor the brain signal oscillation frequency to detect whether or not the oscillation frequency moves from 30 Hz to that of the stimulation frequency (approximately 32 Hz). If the oscillation frequency of the brain signals changes in such a manner, IMD 16 may determine that the brain signals have been entrained by the stimulation, and IMD 16 may than adjust the frequency of the stimulation to change the oscillation frequency of the brain signals.

As will be described further below, processor 40 may adjust the frequency of the delivered electrical stimulation from the first frequency to the second frequency by sweeping and/or stepping the frequency between the first and third frequencies. Processor 40 may sweep the frequency of the delivered electrical stimulation from the first frequency to the second frequency by adjusting the frequency on a substantially continuous basis. Conversely, processor may step the frequency of the delivered electrical stimulation by incrementally adjusting the frequency separated by one or more periods of stimulation at a substantially continuous frequency.

In either case, the adjustment from the first frequency to the third frequency may change the oscillation frequency from that of the second frequency. In some examples, the oscillation frequency may be changed from the second frequency to the third frequency. To treat the patient disorder, the change to the oscillation frequency of the bioelectrical brain signals from the second frequency may be accompanied by a reduction or substantially elimination of the symptoms associated with the second frequency. In some examples, the bioelectrical frequency may change to that of non-pathological brain signals due at least in part to the delivery of electrical stimulation according to the example of FIG. 4.

As an illustration, in the case of Parkinson's disease, processor 40 may control the delivery of electrical stimulation according to the example of FIG. 4 to change the oscillation frequency of the bioelectrical brain signals from the beta frequency range to some other frequency outside the frequency range (e.g., a frequency in the alpha or gamma range). For example, when the bioelectrical brain signals oscillating within the beta range are entrained by the delivered electrical stimulation, processor 40 may adjust the frequency of the delivered electrical stimulation to a frequency in the gamma frequency range (between approximately 35 Hz to approximately 120 Hz). Such an adjustment may cause the bioelectrical brain signals to oscillate at a frequency outside the beta range, e.g., within the gamma frequency range. In some examples, processor 40 may initially deliver electrical stimulation at a frequency in the beta range and, once the bioelectrical brain signals have been entrained, adjust the frequency of the electrical stimulation to a frequency outside the beta range (e.g., to a frequency in the alpha or gamma range) to modulate the oscillation frequency of the bioelectrical brain signals.

In some examples, processor 40 may be configured to perform the example technique of FIG. 4 based at least in part upon the determination that the bioelectrical brain signals are oscillating at the second frequency in one or more regions of interest within brain 28. As will be described with regard to FIG. 5, such a determination may be made by sensing the bioelectrical brain signals of patient 12 via sensing module 46. In some examples, multiple iterations of the technique of FIG. 4 may be performed to ensure that the oscillation frequency of the bioelectrical brain signals of patient 12 are changed from that of the second frequency to a fourth frequency. For example, IMD 16 may deliver and adjust electrical stimulation from the first frequency to the third frequency as shown in FIG. 4 more than once to change the oscillation frequency of the bioelectrical brain signals from the second frequency to the fourth frequency.

FIG. 5 is a flow diagram illustrating another example technique for delivering electrical stimulation therapy via IMD 16 to brain 28 of patient 12. Similar to that of the example of FIG. 4, the electrical stimulation may be delivered to change the oscillation frequency of bioelectrical brain signals in one or more regions of brain 28. As will be described, IMD 16 may deliver such electrical stimulation based at least in part on sensed bioelectrical brain signals of patient 12.

As shown in FIG. 5, processor 40 of IMD 16 may sense bioelectrical brain signals in one or more regions of brain 28 via sensing module 46 and one or more of electrodes 24, 26 (74). For examples in the case of Parkinson's disease, IMD 16 may sense bioelectrical brain signals in subthalamic nucleus (STN), globus pallidus interna (GPi), globus pallidus externa (GPe), and/or other areas of the basal ganglia may be associated with one or more motor symptoms including, e.g., rigidity, akenesia, bradykinesia, diskensia, and/or resting tremor. Examples of the sensed bioelectrical brain signals include, but are not limited to, an electroencephalogram (EEG) signal, an electrocorticogram (ECoG) signal, a local field potential (LFP) sensed from within one or more regions of a patient's brain and/or action potentials from single cells within the patient's brain.

Based on the sensed bioelectrical brain signals, processor 40 may determine whether or not the bioelectrical brain signals exhibit oscillation at a pathological frequency (76). For cases of Parkinson's disease, pathological frequencies may include oscillations in the beta frequency range. Pathological frequencies or frequency ranges may be defined based on the disorder being treated by IMD 16. Again, while examples of the disclosure are primarily focused on oscillations in the beta frequency range to treat Parkinson's disease, other frequencies may be defined as pathological. In some examples, a clinician may define frequency or range of frequencies deemed as pathological in the sense the one or more symptoms of the patient disorder are manifested in combination with oscillation at the one or more frequencies. In some examples, pathological frequencies may be defined on a patient and/or disorder specific basis, and stored in memory 42 of IMD 16 for retrieval by processor 40.

If processor 40 determines that the sensed bioelectrical brain signals do not exhibit oscillations in beta frequency range (or exhibit oscillations below a threshold level in the frequency range) based on the sensed bioelectrical brain signals, processor 40 may not deliver electrical stimulation to entrain the bioelectrical brain signals but may continue to sense the brain signals of patient 12 (74). Conversely, if processor 40 determines that the sensed bioelectrical brain signals exhibit oscillations in the beta frequency range (or exhibit oscillation above a threshold level in the frequency range), processor 40 may deliver electrical stimulation at the first frequency to entrain the bioelectrical brain signals oscillating at the pathological frequency (70), and then adjust the electrical stimulation to a third frequency to change the oscillation frequency of the bioelectrical brain signals (72). IMD 16 may deliver and adjust the electrical stimulation in substantially the same manner described above with regard to the example technique of FIG. 4. Once processor 40 has adjusted the frequency of the electrical stimulation to the third frequency to change the oscillation frequency of the bioelectrical brain signals from that of the pathological frequency, processor 40 may terminate the delivery of the electrical stimulation (82) and continue to sense the bioelectrical brain signals of patient 12 (74) as described above. In some examples, processor 40 may continue to deliver other types of electrical stimulation therapy employed to treat one or more patient disorder despite that fact that the electrical stimulation of FIG. 5 is terminated.

In this manner, IMD 16 may deliver electrical stimulation to one or more regions of brain 28 to modulate the oscillation frequency to that of a frequency different from that of a pathological frequency. The change to the oscillation frequency may result in a reduction or substantially eliminate the manifestation of one or more symptoms associated with bioelectrical brain signals exhibiting oscillations at the pathological frequency or frequencies. Processor 40 may deliver and adjust the delivery of electrical stimulation in this manner based on the determination that the bioelectrical brain signals are oscillating at pathological frequencies. As described above, such a determination may be made by sensing the bioelectrical brain signals at one or more regions of interest within brain 28.

Additionally or alternatively, IMD 16 may be programmed to deliver electrical stimulation in such a manner on a periodic or substantially continuous basis. For example, processor 40 may periodically deliver electric stimulation at one more frequencies to entrain and adjust the oscillation frequencies of bioelectrical brain signals without determining that such bioelectrical brain activity exists, e.g., based on sensed bioelectrical brain signals. In some examples, processor 40 may periodically sweep or step through pathological frequency ranges to entrain bioelectrical brain signals exhibiting oscillation at one more frequencies within the range, and then change the oscillation frequency of such bioelectrical brain signals by adjusting the frequency of the electrical stimulation as described herein. However, as in some instances the delivery of electrical stimulation within a pathological frequency range may serve to induce brain signal activity within such a range if delivered too frequently or for too long, the frequency at which IMD 16 delivers such electrical stimulation may be selected to prevent the inducement of bioelectrical brain activity within the pathological frequency range.

In some examples, prior to terminating the electrical stimulation (82), processor 40 may verify or otherwise determine that the oscillation frequency of the brain signals has changed in the desired manner, e.g., to oscillations at a non-pathological frequency. For example, after adjusting the electrical stimulation from the first frequency to the third frequency, processor 40 may sense the bioelectrical brain signals of patient 12 and determine whether or not the brain signals are still oscillating at a pathological frequency (which may be the same or different than the original pathological frequency that initiated the delivery of electrical stimulation). If processor 40 determines that the brains signals are no longer oscillating at a pathological frequency, processor 40 may then terminate the stimulation (82). If processor 40 determines that the brain signals are still oscillating a pathological frequency, processor 40 may repeat the delivery of electrical stimulation at a frequency selected to entrain the brain signals at the detected oscillation frequency and then adjust the frequency of the stimulation to change the brain signal oscillation frequency. Processor 40 may repeat such a process until the stimulation has successfully changed the oscillation frequency of the brain signals to a desired frequency, e.g., a non-pathological frequency.

Additionally or alternatively, processor 40 may determine whether or not the stimulation has successfully changed the oscillation frequency of the brain signals to a desired frequency, e.g., a non-pathological frequency, by monitoring one or more patient parameters other than that of the oscillating frequency. For example, processor 40 may monitor patient parameters indicated of movement (e.g., via EMG or an accelerometer) to detect whether manifestations of the patient disorder associated with the pathological frequency of the brain signal oscillations have been reduced and/or eliminated in conjunction with the delivery of the electrical stimulation, which may be indicative the brain signals changing to a non-pathological frequency. Once processor 40 determines that monitored patient parameter indicates a reduction or elimination in manifestations, processor 40 may terminate the delivery of electrical stimulation to patient 12.

FIGS. 6A and 6B are graphs illustrating frequency versus time for example bioelectrical brain signals and example electrical stimulation therapy, respectively. In the example of FIGS. 6A and 6B, as well as the remaining figures described below, the oscillation frequency of bioelectrical brain signals is represented by line 84, and the frequency of the electrical stimulation delivered to one or more regions of brain 28 via IMD 16 is represented by line 86. Furthermore, the example of FIGS. 6A and 6B, as well as the remaining figures, illustrate examples in which bioelectrical brain signals oscillating in the beta frequency range may be deemed pathological brain signals, e.g., in the case of Parkinson's disease, and IMD 16 may deliver electrical stimulation therapy to adjust the oscillation frequency to the gamma frequency range (e.g., approximately 75 Hz). However, other oscillation frequencies are contemplated, and may depend on the particular patient disorder being treated by IMD 16.

As shown in FIGS. 6A and 6B, bioelectrical brain signals 84 of patient 12 initially exhibit oscillations in the beta frequency range at approximately 25 Hz. From time T(0) to time T(1), IMD 16 does not deliver electrical stimulation to patient 12 to treat the pathological brain signal oscillations. At time T(1), processor 40 controls stimulation generator 44 to deliver electrical stimulation 86 to one or more regions of brain 28 to entrain the bioelectrical brain signals 84 oscillating at approximately 25 Hz. As indicated in FIG. 6B, processor 40 may control stimulation generator 44 to deliver electrical stimulation 86 defined by a frequency of approximately 25 Hz from time T(1) to time T(2) to entrain the bioelectrical brain signals 84.

As described above, in some examples, the elapsed time between T(1) and T(2) may be approximately 50 milliseconds and approximately 5000 milliseconds, such as, e.g., between approximately 300 milliseconds and approximately 1500 milliseconds. In some examples, the elapsed time between T(1) and T(2) may be at least approximately 50 milliseconds, e.g., for at least 300 milliseconds. In some examples, the elapsed time between T(1) and T(2) may be at least an amount of time approximately equal to at least two periods (e.g., at least three cycles) of the brain signal at the oscillation frequency to be entrained.

At time T(2), processor 40 may begin to increase the frequency of the electrical stimulation 86 delivered to brain 28 from approximately 25 Hz to approximately 75 Hz at time T(3) by sweeping the frequency of the stimulation at a substantially continuous rate. In some examples, processor 40 may adjust the frequency of the electrical stimulation at a rate of approximately 1 Hz to approximately 50 Hz per second. As shown in FIG. 6A, in conjunction with the increase in electrical stimulation frequency, the oscillation frequency of the bioelectrical brain signals also begins to increase at approximately time T(2) and the rate of increase follows substantially the same path as that of the increase in the electrical stimulation frequency. The oscillation frequency of the bioelectrical brain signals 84 increases to approximately 75 Hz at time T(3) at which time the oscillation frequency levels off in conjunction with processor 40 maintaining the delivered electrical stimulation 86 at substantially the same frequency. At time T(4), processor 40 terminates the delivery of electrical stimulation 86 and the bioelectrical brain signals 84 continue to oscillate at approximately 75 Hz. Overall, the electrical stimulation 86 delivered by IMD 16 changes the oscillation frequency of the bioelectrical brain signals 84 from approximately 25 Hz to approximately 75 Hz, which may correspond to a change from a pathological to non-pathological oscillation frequency.

FIGS. 7A and 7B are graphs illustrating frequency versus time for another example of bioelectrical brain signals 84 and example electrical stimulation therapy 86, respectively. The example of FIGS. 7A and 7B is substantially similar to that represented in FIGS. 6A and 6B. However, as shown in FIG. 7B, rather than a sweeping frequency increase, processor 40 increases the frequency of the delivered electrical stimulation 86 from approximately 25 Hz to approximately 75 Hz in a step-wise fashion between time T(2) and time T(3). Processor 40 may make the overall adjustment to the electrical stimulation 86 using any number of steps, which may be substantially the same as each other (e.g., in terms of overall increase of each adjustment and time spent at the continuous rate portion) or may vary. In some examples, processor 40 may adjust the frequency of the delivered electrical stimulation 86 using a combination of steps and sweeps to achieve the overall frequency adjustment to modulate the oscillation frequency of the bioelectrical brain signals as desired.

Similar to that shown in FIG. 6A, the adjustment to the electrical stimulation frequency after the bioelectrical brain signals 84 are entrained causes the oscillation frequency of the bioelectrical brain signals 84 to increase from approximately 25 Hz to approximately 75 Hz. The oscillation frequency of the bioelectrical brain signals 84 is maintained at approximately 75 Hz even after the electrical stimulation in terminated at time T(4). As above, overall, the electrical stimulation 86 delivered by IMD 16 changes the oscillation frequency of the bioelectrical brain signals 84 from approximately 25 Hz to approximately 75 Hz, which may correspond to a change from a pathological to non-pathological oscillation frequency.

FIGS. 8A and 8B are graphs illustrating frequency versus time for another example of bioelectrical brain signals 84 and example electrical stimulation therapy 86, respectively. The example of FIGS. 8A and 8B may be substantially similar to that previously described. For example, overall the oscillation frequency of the bioelectrical brain signals 84 is increased from approximately 25 Hz to approximately 75 Hz. Further, similar to that of FIGS. 7A and 7B, processor 40 adjusts the frequency of the delivered electrical stimulation 86 in a step-wise fashion.

However, unlike that of FIGS. 6B and 7B, processor 40 initiates the delivery of electrical stimulation at a frequency different than that of the oscillation frequency of the bioelectrical brain signal (25 Hz). Instead, processor 40 initially delivers the electrical stimulation 86 at a frequency that, e.g., corresponds to the lower bound of the beta frequency range (e.g., approximately 12 Hz) at time T(1), and then increases the frequency of the electrical stimulation 86 in a step-wise fashion to approximately 75 Hz at time T(4).

As shown, at time T(2) the electrical stimulation 86 is increased to a frequency approximately the same as that of the oscillation frequency of the bioelectrical brain signals, and is maintained at that frequency until time T(3) when processor 40 continues the step-wise increase to the frequency of the electrical stimulation. At time T(3), the bioelectrical brain signals 84 are entrained by the delivered electrical stimulation and, thus, the oscillation frequency of the bioelectrical brain signals increase to approximately 75 Hz at time T(4) in response to the increase in the frequency of the delivered electrical stimulation 86

Such an example process may be utilized, for example, in cases in which IMD 16 in configured to deliver the electrical stimulation periodically rather that in response to the determination that sensed bioelectrical brain signals exhibit oscillation at a frequency within the beta frequency range. Since the electrical stimulation is stepped through substantially all of the beta frequency range, the electrical stimulation may entrain and then increase the oscillation frequency of any bioelectrical brain signals oscillating in the beta frequency range to a frequency outside the beta frequency range. As described above, such a range may be identified as being associated with one or more motor symptoms of Parkinson's disease and changing the oscillation frequency to be outside the beta frequency range may be accompanied by a reduction or elimination in such motor symptoms. In other examples, other frequencies or frequency ranges may be identified as pathological, and processor 40 may be programmed to entrain and modulate bioelectrical brain signals in such a fashion for those pathological frequencies.

Figure 9A:
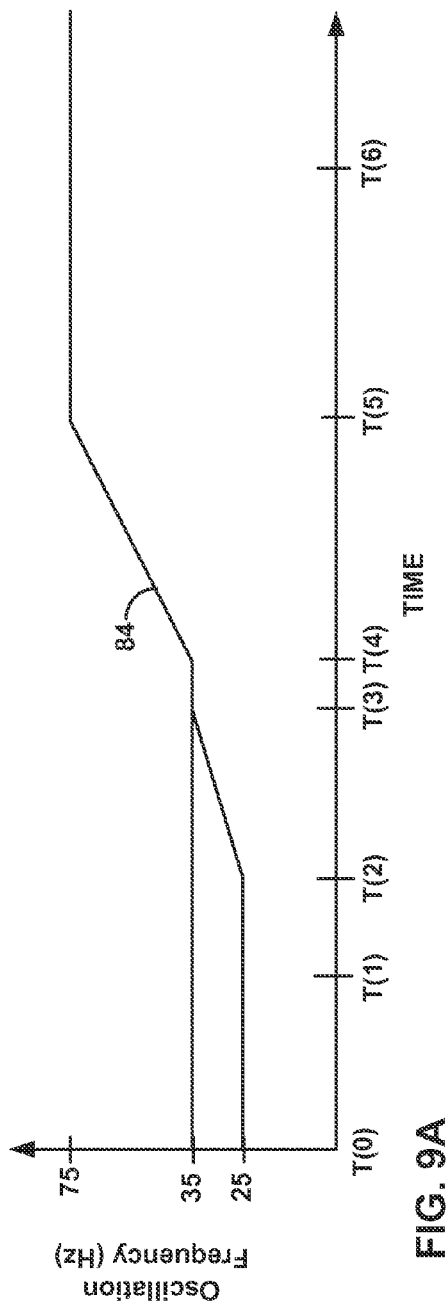
FIGS. 9A and 9B are graphs illustrating frequency versus time for example bioelectrical brain signals and example electrical stimulation therapy, respectively.
Figure 9B:
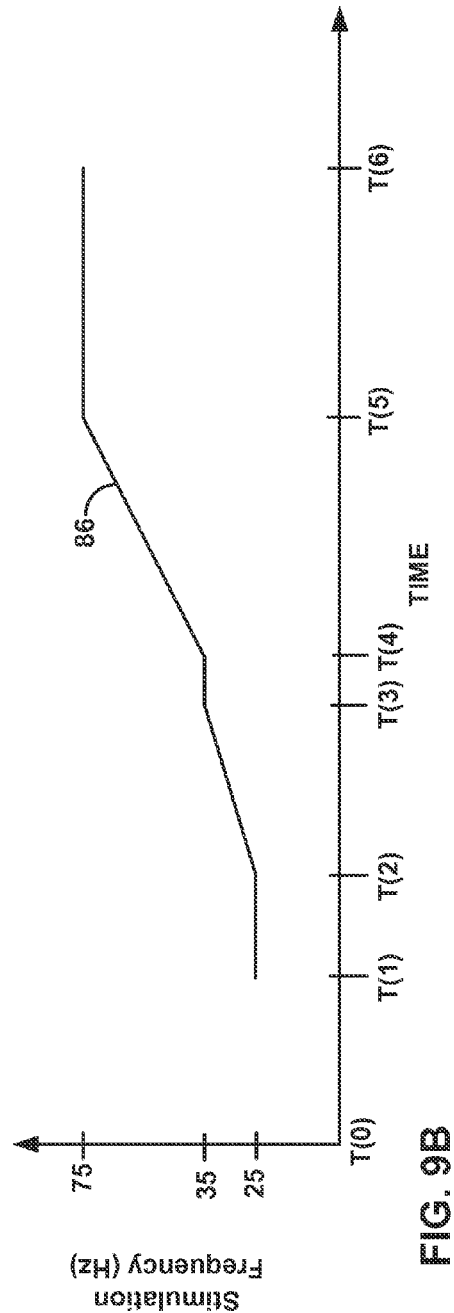

FIGS. 9A and 9B are graphs illustrating frequency versus time for another example of bioelectrical brain signals 84 and example electrical stimulation therapy 86, respectively, Unlike that previously described, the examples of FIGS. 9A and 9B illustrate an example scenario in which oscillations of the bioelectrical brain signals 84 are initially exhibited at multiple frequencies within the beta frequency range. In particular, the bioelectrical brain signals 84 exhibit oscillations at the frequency of approximately 25 Hz and approximately 35 Hz. In some examples, processor 40 may detect the oscillation of the brain signals at one or both of the frequencies based on sensed brain signals and control delivery of the electrical stimulation 86 based on the detection.

As shown in FIG. 9B, processor 40 initiates the delivery of electrical stimulation at time T(1) at a frequency of approximately 25 Hz, and maintains the frequency at approximately 25 Hz until time T(2) to entrain the bioelectrical brain signals oscillating at approximately 25 Hz. At time T(2) processor 40 increases the electrical stimulation frequency to approximately 35 Hz at time T(3). As shown in FIG, 9A, the bioelectrical brain signals 84 oscillating at approximately 25 Hz similarly increase due to the adjustment to the electrical stimulation 86. However, the oscillations at 35 Hz remain at that time. As such, processor 40 maintains the frequency at approximately 35 Hz until time T(4) to entrain the bioelectrical brain signals oscillating at approximately 35 Hz. At time T(4) processor 40 increases the electrical stimulation frequency to approximately 75 Hz at time T(5). As shown in FIG. 9A, the bioelectrical brain signals 84 oscillating at approximately 35 Hz similarly increase due to the adjustment to the electrical stimulation 86. Processor 40 maintains the delivery of electrical stimulation 86 at 75 Hz until time T(6) when the electrical stimulation 86 is terminated. After the electrical stimulation 86 is terminated, the oscillation frequency of the bioelectrical brain signals 84 remains at approximately 75 Hz. Overall, the electrical stimulation 86 delivered by IMD 16 changes the oscillation frequency of the bioelectrical brain signals 84 from approximately 25 Hz and 35 Hz to approximately 75 Hz, which may correspond to a change from two pathological frequencies to a non-pathological oscillation frequency.

Although the examples of FIGS. 6A to 9B are generally described with regard to processor 40 increasing the electrical stimulation to increase the oscillation frequency of the bioelectrical brain signals, in other examples, processor 40 may also decrease the electrical stimulation in a similar fashion to decrease the oscillation frequency of the bioelectrical brain signals. Processor 40 may decrease the frequency of the electrical stimulation to change the oscillation frequency from that of a pathological frequency or frequencies. For example, the decrease in the frequency of the delivered electrical stimulation may cause the oscillation frequency of the bioelectrical brain signals to change from a pathological frequency to a non-pathological frequency. The change to the oscillation frequency may result in a reduction or elimination of one or more symptoms of a patient disorder associated with the pathological frequency.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Various examples of the disclosure have been described. These and other examples are within the scope of the following claims.

The invention claimed is:

1. A method comprising:
 delivering the electrical stimulation from a medical device at a first frequency to a brain of a patient when bioelectrical brain signals of the patient oscillate at a second frequency, wherein the second frequency corresponds to pathological brain signals of the patient, and wherein the electrical stimulation is selected to entrain the bioelectrical brain signals of the patient; and
 adjusting the delivered electrical stimulation from the first frequency to a third frequency while the bioelectrical brain signals are entrained by the electrical stimulation, wherein adjusting the delivered electrical stimulation changes the bioelectrical brain signal oscillations to a fourth frequency different from the second frequency.

2. The method of claim 1, wherein the first frequency is substantially the same as a second frequency.

3. The method of claim 1, wherein the fourth frequency is substantially the same as the third frequency.

4. The method of claim 1, wherein the fourth frequency corresponds to a frequency of non-pathological brain signals of the patient.

5. The method of claim 1, further comprising determining that the bioelectrical brain signals of the patient oscillate at the second frequency, wherein the electrical stimulation is delivered to the brain of the patient based at least in part on the determination.

6. The method of claim 5, wherein determining the bioelectrical brain signals of the patient oscillate at the second frequency comprises:
sensing the bioelectrical brain signals of the patient; and
determining that the bioelectrical brain signals oscillate at the second frequency based on the sensed bioelectrical brain signals.

7. The method of claim 1, wherein adjusting the delivered electrical stimulation from the first frequency to the third frequency comprises sweeping the delivered electrical stimulation from the first therapy to the third frequency.

8. The method of claim 1, wherein adjusting the delivered electrical stimulation from the first frequency to the third frequency comprises stepping the delivered electrical stimulation from the first therapy to the third frequency.

9. The method of claim 1, wherein the second frequency comprises a frequency between approximately 12 Hertz and approximately 35 Hertz.

10. The method of claim 9, wherein the third frequency comprises a frequency between approximately 40 Hertz to approximately 120 Hertz.

11. The method of claim 1, wherein the medical device comprises an implantable medical device.

12. The method of claim 1, further comprising:
sensing the bioelectrical brain signals after adjusting the delivered electrical stimulation from the first frequency to the third frequency; and
determining that the bioelectrical brain signals oscillate at the fourth frequency based on the sensed bioelectrical brain signals.

13. The method of claim 12, further comprising terminating the delivery of electrical stimulation based on the determination that the bioelectrical brain signals oscillate at the fourth frequency.

14. A medical device system comprising:
an electrical stimulation generator configured to generate electrical stimulation; and
a processor configured to control the electrical stimulation generator to generate and deliver the electrical stimulation at a first frequency to a brain of a patient when bioelectrical brain signals of the patient oscillate at a second frequency, wherein the second frequency corresponds to pathological brain signals of the patient, wherein the electrical stimulation is selected to entrain the bioelectrical brain signals of the patient, and adjust the delivered electrical stimulation from the first frequency to a third frequency while the bioelectrical brain signals are entrained by the electrical stimulation, wherein adjusting the delivered electrical stimulation changes the oscillation of the bioelectrical brain signal oscillations to a fourth frequency different from the second frequency.

15. The medical device system of claim 14, wherein the first frequency is substantially the same as the second frequency.

16. The medical device system of claim 14, wherein the fourth frequency is substantially the same as the third frequency.

17. The medical device system of claim 14, wherein the fourth frequency corresponds to a frequency of non-pathological brain signals of the patient.

18. The medical device system of claim 14, wherein the processor is configured to determine that the bioelectrical brain signals of the patient oscillate at the second frequency, wherein the processor controls the electrical stimulation generator to deliver the electrical stimulation at least in part by controlling the electrical stimulation generator to deliver electrical stimulation to the brain of the patient based on the determination.

19. The medical device system of claim 18, further comprising a sensing module configured to sense the bioelectrical brain signals of the patient, wherein the processor determines that the bioelectrical brain signals of the patient oscillate at the second frequency by at least sensing the bioelectrical brain signals of the patient via the sensing module and determining that the bioelectrical brain signals oscillate at the second frequency based on the sensed bioelectrical brain signals.

20. The medical device system of claim 14, wherein the processor is configured to adjust the delivered electrical stimulation from the first frequency to the third frequency by at least sweeping the delivered electrical stimulation from the first frequency to the third frequency.

21. The medical device system of claim 14, wherein the processor is configured to adjust the delivered electrical stimulation from the first frequency to the third frequency by at least stepping the delivered electrical stimulation from the first frequency to the third frequency.

22. The medical device system of claim 14, wherein the second frequency comprises a frequency between approximately 12 Hertz and approximately 35 Hertz.

23. The medical device system of claim 22, wherein the third frequency comprises a frequency between approximately 40 Hertz to approximately 120 Hertz.

24. The medical device system of claim 14, further comprising an implantable medical device, wherein the implantable medical device comprises the processor and the electrical stimulation generator.

25. The medical device system of claim 14, further comprising a sensing module configured to sense the bioelectrical brain signals of the patient, wherein the processor is configured to sense the bioelectrical brain signals after adjusting the delivered electrical stimulation from the first frequency to the third frequency, and determine that the bioelectrical brain signals oscillate at the fourth frequency based on the sensed bioelectrical brain signals.

26. The medical device system of claim 25, wherein the processor is configured to terminate the delivery of electrical stimulation based on the determination that the bioelectrical brain signals oscillate at the fourth frequency.

27. A system comprising:
means for delivering the electrical stimulation at a first frequency to a brain of a patient when bioelectrical brain signals of the patient oscillate at a second frequency, wherein the second frequency corresponds to pathological brain signals of the patient, wherein the electrical stimulation is selected to entrain the bioelectrical brain signals of the patient; and
means for adjusting the delivered electrical stimulation from the first frequency to a third frequency while the bioelectrical brain signals are entrained by the electrical stimulation, wherein the means for adjusting the delivered electrical stimulation changes the bioelectrical brain signal oscillations to a fourth frequency different from the second frequency.

28. A non-transitory computer-readable storage medium comprising instructions that cause one or more processors to:
control delivery of the electrical stimulation at a first frequency to a brain of a patient when bioelectrical brain signals of the patient oscillate at a second frequency, wherein the second frequency corresponds to pathological brain signals of the patient, wherein the electrical stimulation is selected to entrain the bioelectrical brain signals of the patient; and
adjust the delivered electrical stimulation from the first frequency to a third frequency while the bioelectrical brain signals are entrained by the electrical stimulation, wherein adjusting the delivered electrical stimulation changes the bioelectrical brain signal oscillations to a fourth frequency different from the second frequency.

* * * * *